US006676945B2

(12) United States Patent
Laqueyrerie et al.

(10) Patent No.: US 6,676,945 B2
(45) Date of Patent: Jan. 13, 2004

(54) MYCOBACTERIAL PROTEINS, MICROORGANISMS PRODUCING THEM AND THEIR USE FOR VACCINES AND FOR THE DETECTION OF TUBERCULOSIS

(75) Inventors: Anne Laqueyrerie, Paris (FR); Gilles Marchal, Ivry sur Seine (FR); Pascale Pescher, Paris (FR); Felix Romain, Fontenay les Briis (FR)

(73) Assignee: Institut Pasteur, Paris (FR)

( * ) Notice: Subject to any disclaimer, the term of this patent is extended or adjusted under 35 U.S.C. 154(b) by 82 days.

(21) Appl. No.: 09/985,372

(22) Filed: Nov. 2, 2001

(65) Prior Publication Data

US 2003/0054008 A1 Mar. 20, 2003

Related U.S. Application Data

(62) Division of application No. 09/599,366, filed on Jun. 21, 2000, now Pat. No. 6,335,181, which is a division of application No. 09/132,528, filed on Aug. 11, 1998, now Pat. No. 6,221,353, which is a division of application No. 08/641,356, filed on Apr. 30, 1996, now Pat. No. 5,866,130, which is a division of application No. 08/382,184, filed on Feb. 1, 1995, now Pat. No. 5,714,593.

(51) Int. Cl.[7] ................................................ A61K 39/00

(52) U.S. Cl. ................................ 424/192.1; 424/185.1; 424/190.1; 424/192.1; 424/193.1; 424/197.11; 424/201.1; 424/203.1; 424/204.1; 424/217.1; 424/227.1; 424/258.1; 424/245.1; 530/395

(58) Field of Search ................................ 530/350, 395; 424/185.1, 190.1, 192.1, 197.11, 201.1, 203.1, 193.1, 204.1, 217.1, 227.1, 258.1, 245.1

(56) References Cited

U.S. PATENT DOCUMENTS

| | | | |
|---|---|---|---|
| 5,599,541 A | | 2/1997 | Marchal et al. |
| 5,714,593 A | | 2/1998 | Laqueyrerie et al. |
| 5,866,130 A | | 2/1999 | Laqueyrerie et al. |
| 6,060,259 A | * | 5/2000 | Marchal et al. |

FOREIGN PATENT DOCUMENTS

| | | | |
|---|---|---|---|
| WO | WO92/21758 | * | 12/1992 |

OTHER PUBLICATIONS

Wieles et al. Infect. Immun. Jan. 1994. 62(1): 252–258.*

Abou–Zeid et al, "Characterization of the Secreted Antigens of Mycobacterium Bovis BCG: Comparison of the 46–Kilodalton Dimeric Protein with Proteins MPB64 and MPB70", Infection And Immunity, Dec., 1987, vol. 55, No. 12, pp. 3213–3214.

Wiels et al, "Characterization of Mycobacterium Leprae Antigen Related to the Secreted Mycobacterium Tuberculosis Protein MPT32", Infection and Immunity, Jan. 1994, vol. 62, No. 1, pp. 252–258.

Miura et al, "Comparative Studies with Various Substrains of Mycobacterium Bovis BCG on the Production of an Antigenic Protein, MPB70", Infection and Immunity, Feb. 1983, vol. 39, pp. 540–545.

Carlin et al, Monoclonal Antibodies Specific for Elongation Factor TU and Complete Nucleotide Sequence of the TUF Gene in Mycobacterium Tuberculosis, Infection and Immunity, Aug. 1992, vol. 60, No. 8, pp. 3136–3142.

Romain et al. "Identification of a Mycobacterium Bovis BCG 45/47–Kilodalton Antigen Complex, an Immunodominant Targert for Antibody Response After Immunization with Living Bacteria", Infection and Immunity, Feb. 1993, vol. 61, No. 2, pp. 742–750.

Scott B. Snapper et al, Proc. Natl. Acad. Sci. USA, vol. 85, pp. 6987–6991, Sep. 1988, Lysogeny and Transformation in Mycobacteria: Stable Expression of Foreign Genes.

Celeste Yanisch–Perron et al, "Gene", 33 (1988) 103–119, Improved M13 Phage Cloning Vectors and Host Strains: Nucleotide Sequences of the M13mp18 and pUC19 Vectors.

Sambrook, Fritsch and Maniatis, Molecular Cloning, A Laboratory Manual, Second Edition, p. 21.

* cited by examiner

*Primary Examiner*—Jennifer E. Graser
(74) *Attorney, Agent, or Firm*—Oblon, Spivak, McClelland, Maier & Neustadt, P.C.

(57) ABSTRACT

*Mycobacterium tuberculosis* protein having a molecular weight of 28.779 Da, and hybrid proteins containing at least portions of its sequence.

These proteins may in particular be used in vaccines or for the detection of specific tuberculosis antibodies.

12 Claims, 15 Drawing Sheets

●- Supernatant from M. bovis BCG
△- Supernatant from non-transformed M. smegmatis
□- Supernatant from M. smegmatis transformed by a recombinant clone able to express recombinant proteins recognized by the antibodies
▽- Supernatant from M. smegmatis transformed by a recombinant clone not expressing recombinant proteins recognized by the antibodies ▲ – Purified 45/47 kDa proteins
□ – Supernatant from M. smegmatis transformed by pLA1
○ – Supernatant from M. bovis BCG
▽ – Supernatant from non-transformed M. smegmatis mc²155

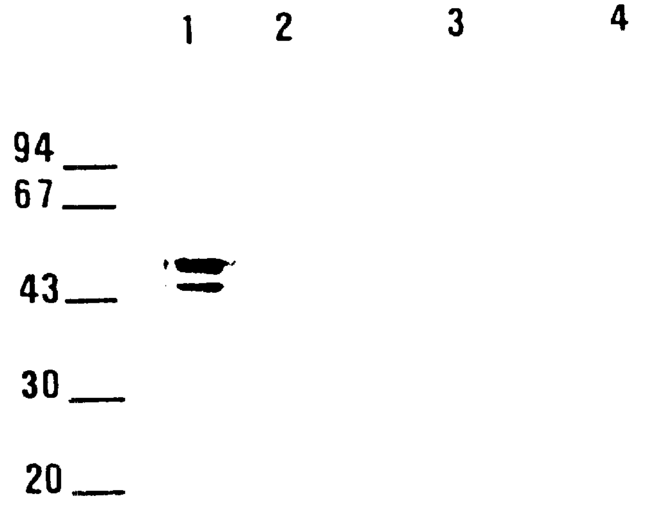
FIGURE 15
FIGURE 16
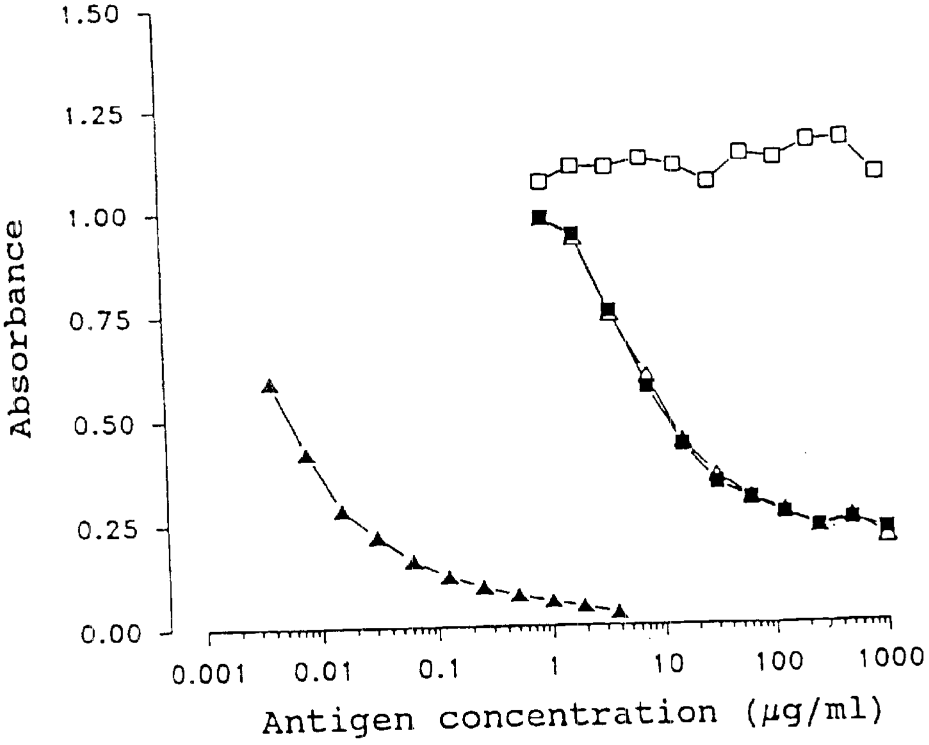
▲ Purified 45/47 kDa proteins
■ Lysate from E. coli XL1-Blue transformed by pLA34
△ Lysate from E. coli XL1-Blue transformed by pLA34-2
□ Lysate from non-transformed E. coli XL1-Blue

```
                        1        10        20        30
SEQ ID2                 MHQVDPNLTRXKGRLAALAIAAMASASLVTVXVPAT
                        |:|||  :  |::||   |  ||||::||||   |::  :|:
mln431    XKNPQPQHKQAVLASQXXHGRFVAMNQVDLDSTHRKGLWAILAIAVVASASAFTMPFRAA·
                  10        20        30        40        50        60

              40        50        60        70        80        90
SEQ ID2   ANADPEPAPPVPTTAASPPSTAAAPPAPATPVAPPPPAAANTPNAQPGDPNAAPPPADPN
          ||||:|         |::     |||||:||:||  ::|  |:|:  :::|||||||| |: |||
mln431    ANADPAPL--------PPSTATAAPSPAQEIITPLPGAPVSSEAQPGDPNA--PSLDPN
                  70        80        90        100

              100       110       120       130       140       150
SEQ ID2   APPPPVIAPNAPQPVRIDNPVGGFSFALPAGWVESDAAHFDYGSALLSKTTGDPPFPGQP
          ||  |  :::|||        ||:|:||||T|:||||||||:|:|:||||:||||:::||  ||f
mln431    APYPLAVDPNA---GRITNAVGGFSFVLPAGWVESEASHLDYGSVLLSKAIEQPPVLGQP
              110       120       130       140       150       160

              160       170       180       190       200       210
SEQ ID2   PPVANDTRIVLGRLDQKLYASAEATDSKAAARLGSDMGEFYMPYPGTRINQETVSLDANG
          : ||:||||||||||||||||||||||::  |||:||||||||||:|||||||||||::|:||+
mln431    TVVATDTRIVLGRLDQKLYASAEADNIKAAVRLGSDMGEFYLPYPGTRINQETIPLHANG
              170       180       190       200       210       220

              220       230       240       250       260       270
SEQ ID2   VSGSASYYEVKFSDPSKPNGQIWTGVIGSPAANAPDAGPPQRWFVVWLGTANNPVDKGAA
          ?:|||||||||||||||:||  |||  |:|:|||||::||:||:|||||||||:|||||||++
mln431    IAGSASYYEVKFSDPNKPIGQICTSVVGSPAASTPDVGPSQRWFVVWLGTSNNPVDKGAA
              230       240       250       260       270       280

              280       290       300       310       320
SEQ ID2   KALAESIRPLVAPPPAPAPAPAEPAPAPAPAGEVAPTPTTPTPQRTLPAX
          |:|||||||:  :||  ||:::|||    ::|
mln431    KELAESIRSEMAPIPASVSAPAPVGXAIRHPLRCHCGPCFLDPPPAEQTTVDNRHSSVYT
              290       300       310       320       330       340
```

FIGURE 17

SEQUENCE LISTING

```
<160> NUMBER OF SEQ ID NOS: 5

<210> SEQ ID NO 1
<211> LENGTH: 2061
<212> TYPE: DNA
<213> ORGANISM: Mycobacterium tuberculosis
<220> FEATURE:
<221> NAME/KEY: CDS
<222> LOCATION: (1082)..(2056)
```

-continued

<400> SEQUENCE: 1

```
gtgctcgggc ccaacggtgc gggcaagtcc accgccctgc atgttatcgc ggggctgctt      60

cgcccccgac gcgggcttgg tacgtttggg ggaccgggtg ttgaccgaca ccgaggccgg     120

ggtgaatgtg gcgacccacg accgtcgagt cgggctgctg ttgcaagacc cgttgttgtt     180

tccacacctg agcgtggcca aaaacgtggc cttcggacca caatgccgtc gcgggatgtt     240

tgggtccggg cgcgcgctag gacaagggcg tcggcactgc gatggctgcg cgaggtgaac     300

gccgagcagt tcgccgaccg taagcctcgt cagctatccg gggccaagc ccagcgcgtc      360

gccatcgcgc gagcgttggc ggccgaaccg gatgtgttgc tgctcgacga gccgctgacc     420

ggactcgatg tggccgcggc cgcgggtatc cgttcggtgt tgcgtagtgt cgtcgcgagg     480

agcggttgcg cggtagtcct gacgacccat gacctgctgg acgtgttcac gctggccgac     540

cgggtattgg tgctcgagtc cggcacgatc gccgagatcg gcccggttgc cgatgtgctt     600

accgcacctc gcagtcgttt cggagcccgt atcgccggag tcaacctggt caatgggacc     660

attggtccgg acggctcgct gcgcacccag tccggcgccc actggtacgg caccccggtc     720

caggatttgc ctactgggca tgaggcaatc gcggtgttcc cgccgacggc ggtggcggtg     780

tatccggaac cgccgcacgg aagcccgcgc aatatcgtcg ggctgacggt ggcggaggtg     840

gatacccgcg gacccacggt cctggtgcgc gggcatgatc agcctggtgg cgcgcctggc     900

cttgccgcat gcatcaccgt cgatgccgcc accgaactgc gtgtggcgcc cggatcgcgc     960

gtgtggttca gcgtcaaggc gcaggaagtg gccctgcacc cggcacccca ccaacacgcc    1020

agttcatgag ccgacccgcg ccgtccttgc gtcgcgccgt taacacggta ggttcttcgc    1080

c atg cat cag gtg gac ccc aac ttg aca cgt cgc aag gga cga ttg gcg    1129
  Met His Gln Val Asp Pro Asn Leu Thr Arg Arg Lys Gly Arg Leu Ala
    1               5                  10                  15

gca ctg gct atc gcg gcg atg gcc agc gcc agc ctg gtg acc gtt gcg     1177
Ala Leu Ala Ile Ala Ala Met Ala Ser Ala Ser Leu Val Thr Val Ala
            20                  25                  30

gtg ccc gcg acc gcc aac gcc gat ccg gag cca gcg ccc ccg gta ccc     1225
Val Pro Ala Thr Ala Asn Ala Asp Pro Glu Pro Ala Pro Pro Val Pro
        35                  40                  45

aca acg gcc gcc tcg ccg ccg tcg acc gct gca gcg cca ccc gca ccg     1273
Thr Thr Ala Ala Ser Pro Pro Ser Thr Ala Ala Ala Pro Pro Ala Pro
    50                  55                  60

gcg aca cct gtt gcc ccc cca cca ccg gcc gcc gcc aac acg ccg aat     1321
Ala Thr Pro Val Ala Pro Pro Pro Pro Ala Ala Ala Asn Thr Pro Asn
 65                  70                  75                  80

gcc cag ccg ggc gat ccc aac gca gca cct ccg ccg gcc gac ccg aac     1369
Ala Gln Pro Gly Asp Pro Asn Ala Ala Pro Pro Pro Ala Asp Pro Asn
                85                  90                  95

gca ccg ccg cca cct gtc att gcc cca aac gca ccc caa cct gtc cgg     1417
Ala Pro Pro Pro Pro Val Ile Ala Pro Asn Ala Pro Gln Pro Val Arg
            100                 105                 110

atc gac aac ccg gtt gga gga ttc agc ttc gcg ctg cct gct ggc tgg     1465
Ile Asp Asn Pro Val Gly Gly Phe Ser Phe Ala Leu Pro Ala Gly Trp
        115                 120                 125

gtg gag tct gac gcc gcc cac ttc gac tac ggt tca gca ctc ctc agc     1513
Val Glu Ser Asp Ala Ala His Phe Asp Tyr Gly Ser Ala Leu Leu Ser
    130                 135                 140

aaa acc acc ggg gac ccg cca ttt ccc gga cag ccg ccg ccg gtg gcc     1561
Lys Thr Thr Gly Asp Pro Pro Phe Pro Gly Gln Pro Pro Pro Val Ala
145                 150                 155                 160

aat gac acc cgt atc gtg ctc ggc cgg cta gac caa aag ctt tac gcc     1609
```

-continued

```
Asn Asp Thr Arg Ile Val Leu Gly Arg Leu Asp Gln Lys Leu Tyr Ala
                165                 170                 175

agc gcc gaa gcc acc gac tcc aag gcc gcg gcc cgg ttg ggc tcg gac      1657
Ser Ala Glu Ala Thr Asp Ser Lys Ala Ala Ala Arg Leu Gly Ser Asp
            180                 185                 190

atg ggt gag ttc tat atg ccc tac ccg ggc acc cgg atc aac cag gaa      1705
Met Gly Glu Phe Tyr Met Pro Tyr Pro Gly Thr Arg Ile Asn Gln Glu
        195                 200                 205

acc gtc tcg ctc gac gcc aac ggg gtg tct gga agc gcg tcg tat tac      1753
Thr Val Ser Leu Asp Ala Asn Gly Val Ser Gly Ser Ala Ser Tyr Tyr
    210                 215                 220

gaa gtc aag ttc agc gat ccg agt aag ccg aac ggc cag atc tgg acg      1801
Glu Val Lys Phe Ser Asp Pro Ser Lys Pro Asn Gly Gln Ile Trp Thr
225                 230                 235                 240

ggc gta atc ggc tcg ccc gcg gcg aac gca ccg gac gcc ggg ccc cct      1849
Gly Val Ile Gly Ser Pro Ala Ala Asn Ala Pro Asp Ala Gly Pro Pro
                245                 250                 255

cag cgc tgg ttt gtg gta tgg ctc ggg acc gcc aac aac ccg gtg gac      1897
Gln Arg Trp Phe Val Val Trp Leu Gly Thr Ala Asn Asn Pro Val Asp
            260                 265                 270

aag ggc gcg gcc aag gcg ctg gcc gaa tcg atc cgg cct ttg gtc gcc      1945
Lys Gly Ala Ala Lys Ala Leu Ala Glu Ser Ile Arg Pro Leu Val Ala
        275                 280                 285

ccg ccg ccg gcg ccg gca ccg gct cct gca gag ccc gct ccg gcg ccg      1993
Pro Pro Pro Ala Pro Ala Pro Ala Pro Ala Glu Pro Ala Pro Ala Pro
    290                 295                 300

gcg ccg gcc ggg gaa gtc gct cct acc ccg acg aca ccg aca ccg cag      2041
Ala Pro Ala Gly Glu Val Ala Pro Thr Pro Thr Thr Pro Thr Pro Gln
305                 310                 315                 320

cgg acc tta ccg gcc tgacc                                            2061
Arg Thr Leu Pro Ala
                325


<210> SEQ ID NO 2
<211> LENGTH: 325
<212> TYPE: PRT
<213> ORGANISM: Mycobacterium tuberculosis

<400> SEQUENCE: 2

Met His Gln Val Asp Pro Asn Leu Thr Arg Arg Lys Gly Arg Leu Ala
  1               5                  10                  15

Ala Leu Ala Ile Ala Ala Met Ala Ser Ala Ser Leu Val Thr Val Ala
            20                  25                  30

Val Pro Ala Thr Ala Asn Ala Asp Pro Glu Pro Ala Pro Pro Val Pro
        35                  40                  45

Thr Thr Ala Ala Ser Pro Pro Ser Thr Ala Ala Ala Pro Pro Ala Pro
     50                  55                  60

Ala Thr Pro Val Ala Pro Pro Pro Pro Ala Ala Ala Asn Thr Pro Asn
 65                  70                  75                  80

Ala Gln Pro Gly Asp Pro Asn Ala Ala Pro Pro Pro Ala Asp Pro Asn
                85                  90                  95

Ala Pro Pro Pro Pro Val Ile Ala Pro Asn Ala Pro Gln Pro Val Arg
            100                 105                 110

Ile Asp Asn Pro Val Gly Gly Phe Ser Phe Ala Leu Pro Ala Gly Trp
        115                 120                 125

Val Glu Ser Asp Ala Ala His Phe Asp Tyr Gly Ser Ala Leu Leu Ser
    130                 135                 140

Lys Thr Thr Gly Asp Pro Pro Phe Pro Gly Gln Pro Pro Pro Val Ala
```

-continued

```
145                 150                 155                 160

Asn Asp Thr Arg Ile Val Leu Gly Arg Leu Asp Gln Lys Leu Tyr Ala
                165                 170                 175

Ser Ala Glu Ala Thr Asp Ser Lys Ala Ala Ala Arg Leu Gly Ser Asp
            180                 185                 190

Met Gly Glu Phe Tyr Met Pro Tyr Pro Gly Thr Arg Ile Asn Gln Glu
        195                 200                 205

Thr Val Ser Leu Asp Ala Asn Gly Val Ser Gly Ser Ala Ser Tyr Tyr
    210                 215                 220

Glu Val Lys Phe Ser Asp Pro Ser Lys Pro Asn Gly Gln Ile Trp Thr
225                 230                 235                 240

Gly Val Ile Gly Ser Pro Ala Ala Asn Ala Pro Asp Ala Gly Pro Pro
                245                 250                 255

Gln Arg Trp Phe Val Val Trp Leu Gly Thr Ala Asn Asn Pro Val Asp
            260                 265                 270

Lys Gly Ala Ala Lys Ala Leu Ala Glu Ser Ile Arg Pro Leu Val Ala
        275                 280                 285

Pro Pro Pro Ala Pro Ala Pro Ala Pro Ala Glu Pro Ala Pro Ala Pro
    290                 295                 300

Ala Pro Ala Gly Glu Val Ala Pro Thr Pro Thr Thr Pro Thr Pro Gln
305                 310                 315                 320

Arg Thr Leu Pro Ala
                325


<210> SEQ ID NO 3
<211> LENGTH: 325
<212> TYPE: PRT
<213> ORGANISM: Mycobacterium tuberculosis

<400> SEQUENCE: 3

Met His Gln Val Asp Pro Asn Leu Thr Arg Arg Lys Gly Arg Leu Ala
  1               5                  10                  15

Ala Leu Ala Ile Ala Ala Met Ala Ser Ala Ser Leu Val Thr Val Ala
             20                  25                  30

Val Pro Ala Thr Ala Asn Ala Asp Pro Glu Pro Ala Pro Pro Val Pro
         35                  40                  45

Thr Thr Ala Ala Ser Pro Pro Ser Thr Ala Ala Ala Pro Pro Ala Pro
     50                  55                  60

Ala Thr Pro Val Ala Pro Pro Pro Pro Ala Ala Ala Asn Thr Pro Asn
 65                  70                  75                  80

Ala Gln Pro Gly Asp Pro Asn Ala Ala Pro Pro Pro Ala Asp Pro Asn
                 85                  90                  95

Ala Pro Pro Pro Pro Val Ile Ala Pro Asn Ala Pro Gln Pro Val Arg
            100                 105                 110

Ile Asp Asn Pro Val Gly Gly Phe Ser Phe Ala Leu Pro Ala Gly Trp
        115                 120                 125

Val Glu Ser Asp Ala Ala His Phe Asp Tyr Gly Ser Ala Leu Leu Ser
    130                 135                 140

Lys Thr Thr Gly Asp Pro Pro Phe Pro Gly Gln Pro Pro Pro Val Ala
145                 150                 155                 160

Asn Asp Thr Arg Ile Val Leu Gly Arg Leu Asp Gln Lys Leu Tyr Ala
                165                 170                 175

Ser Ala Glu Ala Thr Asp Ser Lys Ala Ala Ala Arg Leu Gly Ser Asp
            180                 185                 190
```

-continued

```
Met Gly Glu Phe Tyr Met Pro Tyr Pro Gly Thr Arg Ile Asn Gln Glu
        195                 200                 205

Thr Val Ser Leu Asp Ala Asn Gly Val Ser Gly Ser Ala Ser Tyr Tyr
    210                 215                 220

Glu Val Lys Phe Ser Asp Pro Ser Lys Pro Asn Gly Gln Ile Trp Thr
225                 230                 235                 240

Gly Val Ile Gly Ser Pro Ala Ala Asn Ala Pro Asp Ala Gly Pro Pro
                245                 250                 255

Gln Arg Trp Phe Val Val Trp Leu Gly Thr Ala Asn Asn Pro Val Asp
            260                 265                 270

Lys Gly Ala Ala Lys Ala Leu Ala Glu Ser Ile Arg Pro Leu Val Ala
        275                 280                 285

Pro Pro Pro Ala Pro Ala Pro Ala Pro Ala Glu Pro Ala Pro Ala Pro
    290                 295                 300

Ala Pro Ala Gly Glu Val Ala Pro Thr Pro Thr Thr Pro Thr Pro Gln
305                 310                 315                 320

Arg Thr Leu Pro Ala
                325


<210> SEQ ID NO 4
<211> LENGTH: 286
<212> TYPE: PRT
<213> ORGANISM: Mycobacterium tuberculosis

<400> SEQUENCE: 4

Asp Pro Glu Pro Ala Pro Pro Val Pro Thr Thr Ala Ala Ser Pro Pro
  1               5                  10                  15

Ser Thr Ala Ala Ala Pro Pro Ala Pro Ala Thr Pro Val Ala Pro Pro
            20                  25                  30

Pro Pro Ala Ala Ala Asn Thr Pro Asn Ala Gln Pro Gly Asp Pro Asn
        35                  40                  45

Ala Ala Pro Pro Pro Ala Asp Pro Asn Ala Pro Pro Pro Pro Val Ile
     50                  55                  60

Ala Pro Asn Ala Pro Gln Pro Val Arg Ile Asp Asn Pro Val Gly Gly
 65                  70                  75                  80

Phe Ser Phe Ala Leu Pro Ala Gly Trp Val Glu Ser Asp Ala Ala His
                 85                  90                  95

Phe Asp Tyr Gly Ser Ala Leu Leu Ser Lys Thr Thr Gly Asp Pro Pro
            100                 105                 110

Phe Pro Gly Gln Pro Pro Pro Val Ala Asn Asp Thr Arg Ile Val Leu
        115                 120                 125

Gly Arg Leu Asp Gln Lys Leu Tyr Ala Ser Ala Glu Ala Thr Asp Ser
    130                 135                 140

Lys Ala Ala Ala Arg Leu Gly Ser Asp Met Gly Glu Phe Tyr Met Pro
145                 150                 155                 160

Tyr Pro Gly Thr Arg Ile Asn Gln Glu Thr Val Ser Leu Asp Ala Asn
                165                 170                 175

Gly Val Ser Gly Ser Ala Ser Tyr Tyr Glu Val Lys Phe Ser Asp Pro
            180                 185                 190

Ser Lys Pro Asn Gly Gln Ile Trp Thr Gly Val Ile Gly Ser Pro Ala
        195                 200                 205

Ala Asn Ala Pro Asp Ala Gly Pro Pro Gln Arg Trp Phe Val Val Trp
    210                 215                 220

Leu Gly Thr Ala Asn Asn Pro Val Asp Lys Gly Ala Ala Lys Ala Leu
225                 230                 235                 240
```

-continued

```
Ala Glu Ser Ile Arg Pro Leu Val Ala Pro Pro Pro Ala Pro Ala Pro
                245                 250                 255

Ala Pro Ala Glu Pro Ala Pro Ala Pro Ala Pro Ala Gly Glu Val Ala
            260                 265                 270

Pro Thr Pro Thr Thr Pro Thr Pro Gln Arg Thr Leu Pro Ala
        275                 280                 285


<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence:peptide

<400> SEQUENCE: 5

Ala Pro Glu Pro Ala Pro Pro Val Pro Pro Ala Ala Ala Ala Pro Pro
  1               5                  10                  15

Ala
```

MYCOBACTERIAL PROTEINS, MICROORGANISMS PRODUCING THEM AND THEIR USE FOR VACCINES AND FOR THE DETECTION OF TUBERCULOSIS

The Present application is a Divisional Application of U.S. Ser. No. 09/599,366 filed Jun. 21, 2000, now U.S. Pat. No. 6,335,181, which is a Divisional of U.S. application Ser. No. 09/132,528 filed Aug. 11, 1998, now U.S. Pat. No. 6,221,353, which is a divisional of application Ser. No. 08/641,356 filed Apr. 30, 1996, now U.S. Pat. No. 5,866, 130, which is a divisional of U.S. Ser. No. 08/382,184 filed Feb. 1, 1995, now U.S. Pat. No. 5,714,593.

The object of the present invention is mycobacterial proteins and microorganisms producing them.

It also relates to the use of these proteins in vaccines or for the detection of *tuberculosis.*

*Tuberculosis* continues to be a public health problem throughout the world. The annual number of deaths directly related to *tuberculosis* is about 3 million and the number of new cases of *tuberculosis* is about 15 million. This number of deaths due to *tuberculosis* is high even for the developed countries; for example in France it is of the order of 1500 per year, a figure which is certainly underestimated by a factor of 2 or 3 if Roujeau's assessments of the differences between official figures and the results of systematic autopsies are taken into account. The recent increase in *tuberculosis* cases, or at least the levelling-off of the decrease in the frequency of this disease, must be considered in correlation with the development of the HIV/AIDS epidemic. In total, *tuberculosis* remains the leading infectious disease in terms of frequency in France and the developed countries, but above all in the developing countries for which it constitutes the principal source of human loss related to a single disease.

At present, a definite diagnosis made by the demonstration of cultivatable bacilli in a sample taken from the patient is only obtained in less than half the cases of *tuberculosis.* Even for pulmonary *tuberculosis*, which represents 80 to 90% of the *tuberculosis* cases, and which is the form of the disease for which the detection of the bacilli is the easiest, the examination of expectorations is only positive for less than half the cases.

The development of more sensitive techniques such as PCR (amplification by polymerase chain reaction), always comes up against the necessity for obtaining a sample. Women and children do not normally spit, and samples for infants frequently require relatively specialized medical intervention (for example ganglionic biopsy or sampling by lumbar puncture of the cephalorachidian fluid).

In other respects, inhibitions of the PCR reaction itself exist, of a type such that a sample may be unusable by this technique because of the impossibility of controlling its origins.

Finally, because of its limits of sensitivity (at the best of the order of $10^4$ to $10^5$ bacilli in the sample) the classic bacteriological diagnosis, microscopic examination and culture, requires that there has already been a relatively substantial development of bacilli and thus of the disease.

The detection of specific antibodies directed against *Mycobacterium tuberculosis* should thus be of assistance in the diagnosis of the common forms of the disease for which the detection of the bacilli themselves is difficult or impossible.

Successive generations of research workers have attempted to perfect a serological diagnostic technique for *tuberculosis.*

For a general review of studies carried out in this area, the application PCT WO-92/21758 may advantageously be referred to.

The techniques reported in the prior art are thus largely based on the preliminary isolation of proteins through their biochemical properties. It is not until after this isolation that the authors have tested the capacity of these proteins to detect those individuals affected by *tuberculosis.*

Application PCT WO-92/21758 describes a method for unambiguously selecting representative antigens of tubercular infection using serums originating from patients affected by *tuberculosis* or guinea-pigs immunized by live bacilli. This method, which is distinguished from the majority of the experiments described in the prior art, has led to the isolation of *M.bovis* proteins with molecular weights between 44.5 and 47.5 kD.

The seventeen amino acids of the N-terminal of one of these proteins were determined and are the following: (SEQ ID NO:5)

```
ALA-PRO-GLU-PRO-ALA-PRO-PRO-VAL-PRO-PRO-ALA-ALA-
 1   2   3   4   5   6   7   8   9  10  11  12

ALA-ALA-PRO-PRO-ALA
15  16  17
```

The article by ROMAIN et al. (1993, Infection and immunity, 61, 742–750) recapitulates the substance of the results described in this international application. It more particularly describes a competitive ELISA assay using a rabbit polyclonal immune serum obtained by immunizing rabbits against the 45–47 kD protein complex described above.

In parallel, a gene library from *Mycobacterium tuberculosis* has been created by JACOBS et al. (1991, Methods Enzymol., 204, 537–557).

This library contains a large number of different clones.

A protein from another Mycobacteria species, *M. leprae*, has moreover been identified by WIELES et al. (1994, Infection and Immunity, 62, 252–258). This protein, named 43 L, has a molecular weight deduced from the nucleotide sequence of about 25.5 Da. Its N-terminal has 47% homology with that of the 45–47 kDa protein complex identified in *Mycobacterium bovis* BCG, and whose 17 amino acid sequence is given above.

As stated above, there is a major interest in human medicine, as much from the therapeutic as the diagnostic point of view, in accurately identifying the proteins produced by the Mycobacteria and in particular by *M. tuberculosis.*

The problem which is in fact posed and is as yet unresolved lies in obtaining vaccines against a large number of diseases.

Another problem lies in the detection of diseases induced by the Mycobacteria, such as *tuberculosis.*

The applicant has thus pursued the determination of the sequence of a *Mycobacterium tuberculosis* protein, which is suspected of playing a major role in the immune response.

The applicant has demonstrated that the group of proteins corresponding to the 45–47 kD complex described above is coded by one and the same gene, and that the calculated molecular mass is different from the molecular mass estimated on polyacrylamide gel, because of its richness in proline.

The object of the present invention is thus a protein having at least a portion of one of the following sequences SEQ ID No2 or SEQ ID No3:

SEQ ID No2:

Met His Gln Val Asp Pro Asn Leu Thr Arg Arg Lys Gly Arg Leu Ala Ala Leu Ala Ile Ala Ala Met Ala Ser Ala Ser Leu Val Thr Val Ala Val Pro Ala Thr Ala Asn Ala Asp Pro Glu Pro

Ala Pro Pro Val Pro Thr Thr Ala Ala Ser Pro Pro Ser Thr Ala Ala Ala Pro Pro Ala Pro Ala Thr Pro Val Ala Pro Pro Pro Pro Ala Ala Ala Asn Thr Pro Asn Ala Gln Pro Gly Asp Pro Asn Ala Ala Pro Pro Pro Ala Asp Pro Asn Ala Pro Pro Pro Pro Val Ile Ala Pro Asn Ala Pro Gln Pro Val Arg Ile Asp Asn Pro Val Gly Gly Phe Ser Phe Ala Leu Pro Ala Gly Trp Val Glu Ser Asp Ala Ala His Phe Asp Tyr Gly Ser Ala Leu Leu Ser Lys Thr Thr Gly Asp Pro Pro Phe Pro Gly Gln Pro Pro Pro Val Ala Asn Asp Thr Arg Ile Val Leu Gly Arg Leu Asp Gln Lys Leu Tyr Ala Ser Ala Glu Ala Thr Asp Ser Lys Ala Ala Ala Arg Leu Gly Ser Asp Met Gly Glu Phe Tyr Met Pro Tyr Pro Gly Thr Arg Ile Asn Gln Glu Thr Val Ser Leu Asp Ala Asn Gly Val Ser Gly Ser Ala Ser Tyr Tyr Glu Val Lys Phe Ser Asp Pro Ser Lys Pro Asn Gly Gln Ile Trp Thr Gly Val Ile Gly Ser Pro Ala Ala Asn Ala Pro Asp Ala Gly Pro Pro Gln Arg Trp Phe Val Val Trp Leu Gly Thr Ala Asn Asn Pro Val Asp Lys Gly Ala Ala Lys Ala Leu Ala Glu Ser Ile Arg Pro Leu Val Ala Pro Pro Pro Ala Pro Ala Pro Ala Pro Ala Glu Pro Ala Pro Ala Pro Ala Pro Ala Gly Glu Val Ala Pro Thr Pro Thr Thr Pro Thr Pro Gln Arg Thr Leu Pro Ala

SEQ ID No3:

Asp Pro Glu Pro Ala Pro Pro Val Pro Thr Thr Ala Ala Ser Pro Pro Ser Thr Ala Ala Ala Pro Pro Ala Pro Ala Thr Pro Val Ala Pro Pro Pro Pro Ala Ala Ala Asn Thr Pro Asn Ala Gln Pro Gly Asp Pro Asn Ala Ala Pro Pro Pro Ala Asp Pro Asn Ala Pro Pro Pro Pro Val Ile Ala Pro Asn Ala Pro Gln Pro Val Arg Ile Asp Asn Pro Val Gly Gly Phe Ser Phe Ala Leu Pro Ala Gly Trp Val Glu Ser Asp Ala Ala His Phe Asp Tyr Gly Ser Ala Leu Leu Ser Lys Thr Thr Gly Asp Pro Pro Phe Pro Gly Gln Pro Pro Pro Val Ala Asn Asp Thr Arg Ile Val Leu Gly Arg Leu Asp Gln Lys Leu Tyr Ala Ser Ala Glu Ala Thr Asp Ser Lys Ala Ala Ala Arg Leu Gly Ser Asp Met Gly Glu Phe Tyr Met Pro Tyr Pro Gly Thr Arg Ile Asn Gln Glu Thr Val Ser Leu Asp Ala Asn Gly Val Ser Gly Ser Ala Ser Tyr Tyr Glu Val Lys Phe Ser Asp Pro Ser Lys Pro Asn Gly Gln Ile Trp Thr Gly Val Ile Gly Ser Pro Ala Ala Asn Ala Pro Asp Ala Gly Pro Pro Gln Arg Trp Phe Val Val Trp Leu Gly Thr Ala Asn Asn Pro Val Asp Lys Gly Ala Ala Lys Ala Leu Ala Glu Ser Ile Arg Pro Leu Val Ala Pro Pro Pro Ala Pro Ala Pro Ala Pro Ala Glu Pro Ala Pro Ala Pro Ala Pro Ala Gly Glu Val Ala Pro Thr Pro Thr Thr Pro Thr Pro Gln Arg Thr Leu Pro Ala

The invention also relates to hybrid proteins having at least a portion of the sequence SEQ ID No2 or SEQ ID No3 and a sequence of a peptide or a protein able to induce an immune response in man or in animals.

Advantageously, the antigenic determinant is such that it is able to induce a humoral and/or cellular response.

Such a determinant may be of a diverse nature and notably an antigenic protein fragment, advantageously a glycoprotein, utilized in order to obtain immunogenic compositions able to induce the synthesis of antibodies directed against multiple epitopes.

These hybrid molecules may also be constituted in part by a molecule carrying the sequences SEQ ID No2 or SEQ ID No3 combined with a portion, in particular an epitope, of diphtheria toxin, tetanus toxin, the HBS antigen of the HBV virus, the VP1 antigen of the poliomyelitis virus or any other viral toxin or antigen.

The processes for synthesizing the hybrid molecules include the methods used in genetic engineering for producing hybrid DNA coding for the required protein or peptide sequences.

The present invention also includes proteins having secondary differences or limited variations in their amino acid sequences which do not functionally modify them by comparison with the proteins having the sequences SEQ ID No2 and SEQ ID No3, or with hybrid proteins containing at least a portion of these sequences.

It should be noted that the present invention has revealed a very large difference in molecular weight between the weights calculated for the protein corresponding to the sequence SEQ ID No3, which is of 28779 Da, and that of the complex, evaluated by SDS gel, which is of the order of 45–47 kD. This difference is probably due to the high frequency (21.7%) of proline in the polypeptide chain.

Other objects of the invention are oligonucleotides, RNA or DNA, coding for the proteins defined above. One such nucleotide has advantageously at least a portion of the following SEQ ID No1:

```
Met His Gln Val Asp Pro Asn Leu Thr  SEQ ID N" 2:
Arg Arg Lys Gly Arg Leu Ala Ala Leu
Ala Ile Ala Ala Met Ala Ser Ala Ser
Leu Val Thr Val Ala Val Pro Ala Thr
Ala Asn Ala Asp Pro Glu Pro Ala Pro
Pro Val Pro Thr Thr Ala Ala Ser Pro
Pro Ser Thr Ala Ala Ala Pro Pro Ala
Pro Ala Thr Pro Val Ala Pro Pro Pro
Pro Ala Ala Ala Asn Thr Pro Asn Ala
Gln Pro Gly Asp Pro Asn Ala Ala Pro
Pro Pro Ala Asp Pro Asn Ala Pro Pro
Pro Pro Val Ile Ala Pro Asn Ala Pro
Gln Pro Val Arg Ile Asp Asn Pro Val
Gly Gly Phe Ser Phe Ala Leu Pro Ala
Gly Trp Val Glu Ser Asp Ala Ala His
Phe Asp Tyr Gly Ser Ala Leu Leu Ser
Lys Thr Thr Gly Asp Pro Pro Phe Pro
Gly Gln Pro Pro Pro Val Ala Asn Asp
Thr Arg Ile Val Leu Gly Arg Leu Asp
Gln Lys Leu Tyr Ala Ser Ala Glu Ala
Thr Asp Ser Lys Ala Ala Ala Arg Leu
Gly Ser Asp Met Gly Glu Phe Tyr Met
Pro Tyr Pro Gly Thr Arq Ile Asn Gln
Glu Thr Val Ser Leu Asp Ala Asn Gly
Val Ser Gly Ser Ala Ser Tyr Tyr Glu
Val Lys Phe Ser Asp Pro Ser Lys Pro
Asn Gly Gln Ile Trp Thr Gly Val Ile
Gly Ser Pro Ala Ala Asn Ala Pro Asp
Ala Gly Pro Pro Gln Arg Trp Phe Val
Val Trp Leu Gly Thr Ala Asn Asn Pro
Val Asp Lys Gly Ala Ala Lys Ala Leu
Ala Glu Ser Ile Arq Pro Leu Val Ala
```

-continued

```
Pro Pro Pro Ala Pro Ala Pro Ala Pro

Ala Glu Pro Ala Pro Ala Pro Ala Pro

Ala Gly Glu Val Ala Pro Thr Pro Thr

Thr Pro Thr Pro Gln Arg Thr Leu Pro

Ala
```

The present invention also relates to a microorganism producing one of the proteins such as are described above and in particular a microorganism secreting such an protein.

The microorganism is preferentially a bacterium such as *Mycobacterium bovis* BCG. These bacteria are already used in man in order to obtain an immunity against *tuberculosis*.

The production of hybrid proteins according to the present invention in *M. bovis* BCG has specific advantages. *M. bovis* BCG is a strain widely used for vaccination purposes and which is accepted as being innocuous to man. After injection into the human body it develops slowly over 15 days to 1 month, which leads to excellent presentation of the antigen against which a response is desired from the organism.

On the other hand *Mycobacterium leprae*, which is the agent of leprosy in man, is little known. This bacterium has not up till now been able to be cultivated on a culture medium and has a very long growth period by comparison with *M. bovis*.

Its potential pathogenicity is moreover an obvious argument for not using it for vaccination purposes.

Proteins with the sequences SEQ ID No2 or SEQ ID No3 have the advantage of being recognized by the antibody present in *tuberculosis*patients and thus constitute a priori highly immunogenic antigens.

The proteins originate from *M. tuberculosis*, which is a species very close to *M. bovis*, these two bacteria being responsible for *tuberculosis* in man and cattle respectively.

The proteins originating from *M. tuberculosis* are thus able to be expressed in *M. bovis* and to be excreted in the culture medium by cells possessing a signal peptide.

Since *M. bovis* has the advantages listed above for vaccination in man and since in addition the proteins corresponding to the SEQ ID No2 and SEQ ID No3 sequences induce a strong immune response in man, it is especially advantageous to produce hybrid proteins in *M. bovis* which carry a portion of the proteins originating from *M. tuberculosis*.

It is well known that the pathogenic microbial antigens against which a vaccination is being sought can only induce a very weak response in man unless they are presented in a specific manner.

The present invention resolves this problem in two ways:

on the one hand by presenting the hybrid protein on the surface of *M. bovis* BCG, and/or excreted by the bacteria, and on the other by combining an antigenic determinant known to induce a strong immune response, i.e. the antigenic determinant of one of the proteins with SEQ ID No2 or SEQ ID No3, with an antigenic determinant inducing a weak response when it is injected alone.

The combination of the antigenic determinant of one of the proteins SEQ ID No2 or SEQ ID No3 allows an amplification of the immune response against the second antigenic determinant of the hybrid protein. This phenomenon can perhaps be compared to the hapten carrier effect.

It is clear that such an operation cannot be envisaged with a protein originating from *M. leprae*, such as that described in the article by WIELES et al. (1994, cited above), since on the one hand because of the much larger difference between *M. tuberculosis* and *M. leprae*, such a protein might not be properly expressed, and on another the immune response induced by this *M. leprae* protein is less well known. In addition the introduction of a protein from a pathogenic species for vaccination purposes constitutes a potential risk to human health which the pharmaceutical industry is reluctant to accept.

All these arguments contribute to a distinction between the protein sequences SEQ ID No2 and SEQ ID No3 and the *M. leprae* protein described by WIELES et al. (1994, cited above), despite their apparent sequence homologies (see later in FIG. 17).

The present invention also relates to vaccines or drugs containing at least one protein or microorganism such as those previously defined.

Vaccines containing nongrafted proteins may be used to immunize individuals against *tuberculosis*. Grafted proteins carrying an epitope originating from a biological agent other than *M. bovis* may be used for immunization against other diseases.

As an indication, 1 to 500 μg of protein per dose for an individual, or $10^3$ to $10^7$ recombinant bacteria per individual, may be used intradermally.

Another object of the present invention is a pharmaceutical composition containing at least a pharmaceutically effective quantity of a protein or a microorganism such as previously described in combination with pharmaceutically compatible diluents or adjuvants.

Another object of the present invention is a process for detecting the specific *tuberculosis* antibodies, in which a biological fluid, in which the presence of said antibodies is sought, is brought into contact with a protein such as that described above.

Advantageously, said protein is fixed on a support.

Such detection could in particular be implemented by the Western-Blot (immuno-imprint) method, by an enzyme immunoassay method (ELISA) or a radioimmunoassay method (RIA), by use of an assay kit, containing the proteins as well as in particular buffer solutions allowing the immunological reaction to be carried out and if necessary substances allowing the antibody-antigen complex formed to be revealed.

The present invention is illustrated without in any way being restricted by the following examples and the annexed drawings in which.

Figure 1:
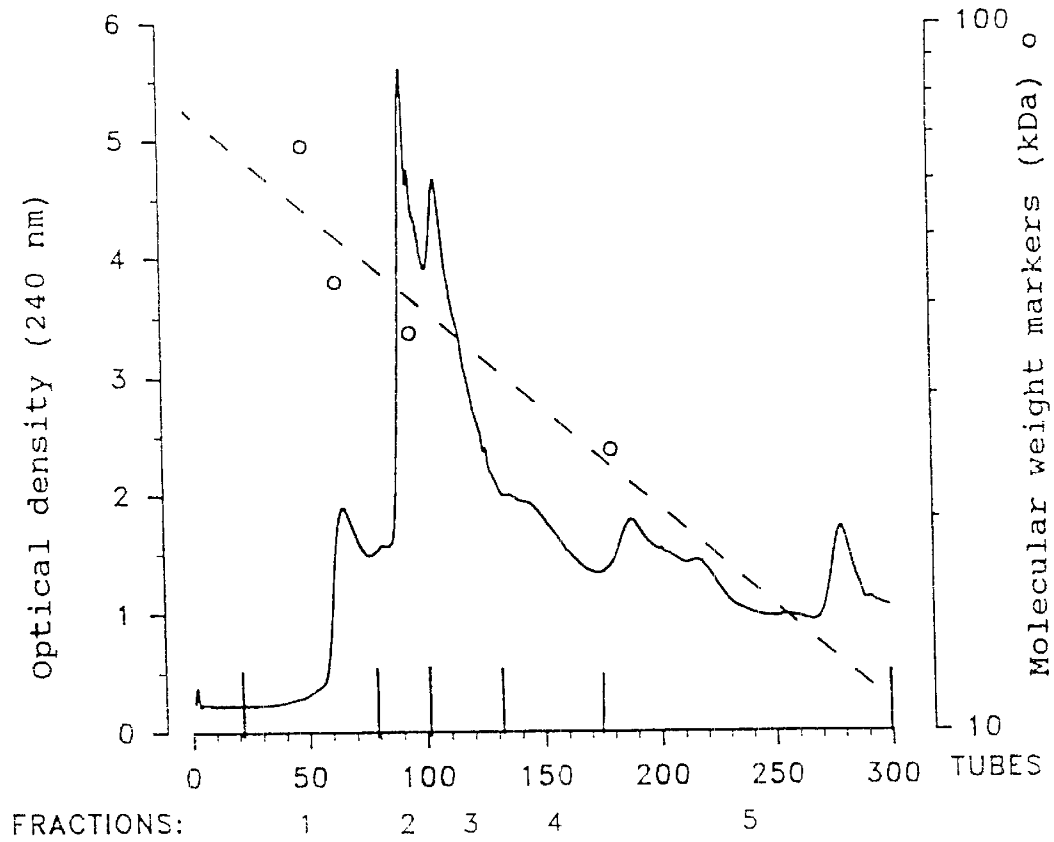
FIG. 1 is an optical density (OD) profile at 240 nm of the molecular filtration (Si 300) of an *M. tuberculosis* fraction not retained on an ion-exchange column under the conditions described later.

- a colorant for molecules (4A) transferred on the PVDF membrane. Aurodye coloration (Amersham);
- a mixture of serums from guinea-pigs immunized with live (4B) or dead (4C) bacilli;
- a serum (4D) from rabbit immunized with purified antigens from BCG (Infection and Immunity (1993) 61 742–750);
- a monoclonal antibody reference I-1081 (4E).

These PVDF membranes had previously received the molecules from fractions separated on the low-pressure ion-exchange column separated by electrophoresis on acrylamide gel. Track 0 corresponds to the raw starting material, track 1 to the non-retained fraction, and track 2 to the fraction retained.

FIG. 5A to 5E represent PVDF membranes corresponding to a gel obtained by the migration of the 5 fractions (1 to 5) obtained on the Si 300 gel filtration column and the non-retained fraction from the low-pressure DEAE column (0). After transfer of identical gels on PVDF membranes one was revealed by use of a protein colorant ([Aurodye, Amersham (5A)], or a serum from guinea-pigs immunized with live (5B) or dead (5C) bacilli, or a rabbit serum (5D) or a monoclonal antibody (5E).

FIGS. 6A to 6E show PVDF membranes corresponding to a gel obtained by the migration of fractions obtained on a high-pressure ion-exchange column (1 to 3) and fraction 1 obtained by filtration on a molecular sieve (well 0), said membrane being revealed:

by a protein colorant (6A), by an antibody from the serum of guinea-pigs immunized with respectively live (6B) or dead (6C) bacilli, by a rabbit serum (6D);

by a monoclonal antibody (6E).

FIGS. 7A to 7D show the imprint of gels on membranes corresponding to the migration of the fraction 1 obtained on ion-exchange column (0) and the fractions obtained by reversed phase chromatography (1 to 5), revealed by the same reagents as for FIGS. 6A to 6B, 6D to 6E with the same codes.

Figure 8:
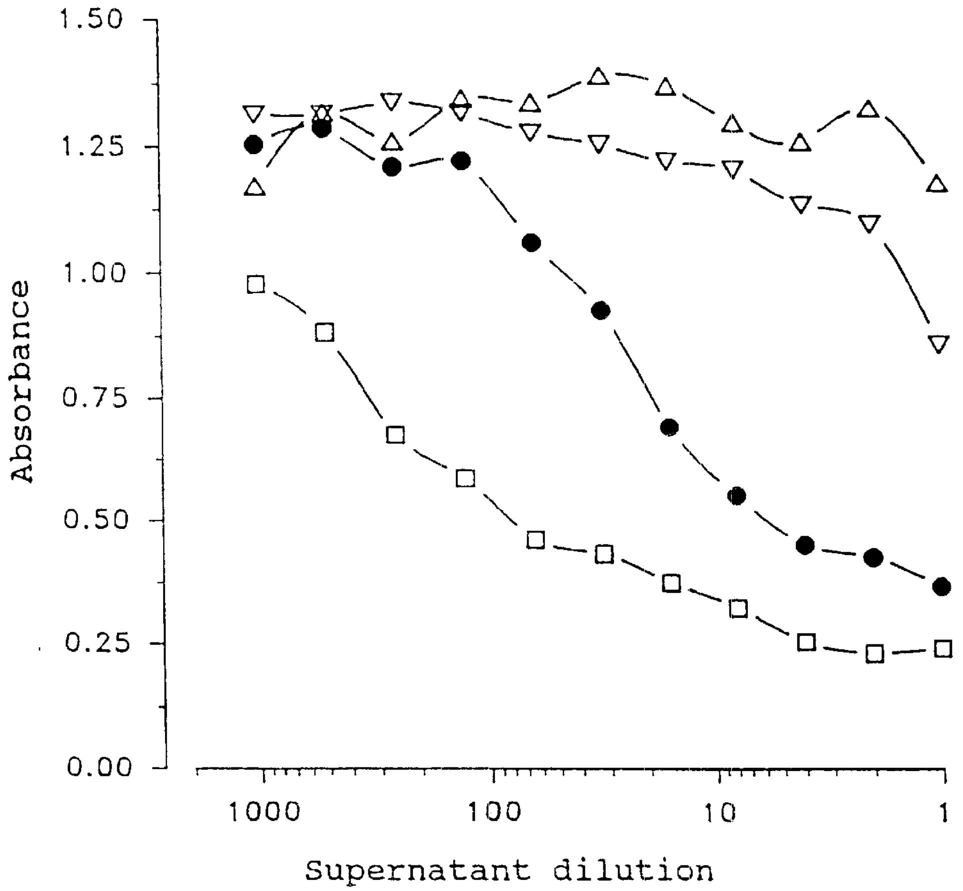

FIG. 8 shows the screening of the gene library for the expression of *M. tuberculosis* H37Rv in *M. smegmatis*. The supernatants of *M. bovis* BCG, non-transformed *M. smegmatis* and *M. smegmatis* transformed by the recombinant clones expressing or not expressing the recombinant proteins recognized by the antibodies, were tested at different dilutions.

Figure 9:
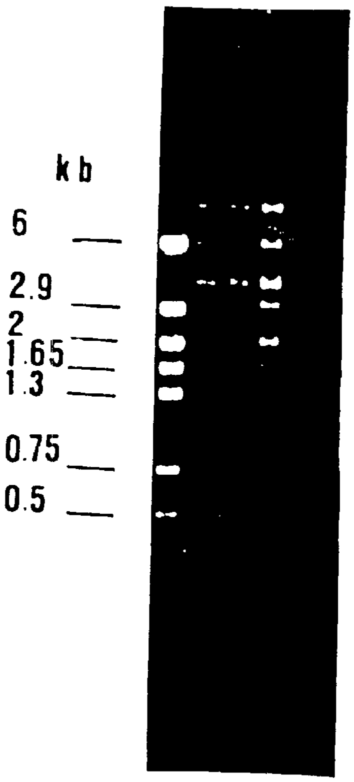

FIG. 9 shows the migration in agarose gel of three cosmids selected from the library, electropored in *E. coli* and extracted by alkaline lysis.

Figure 10:
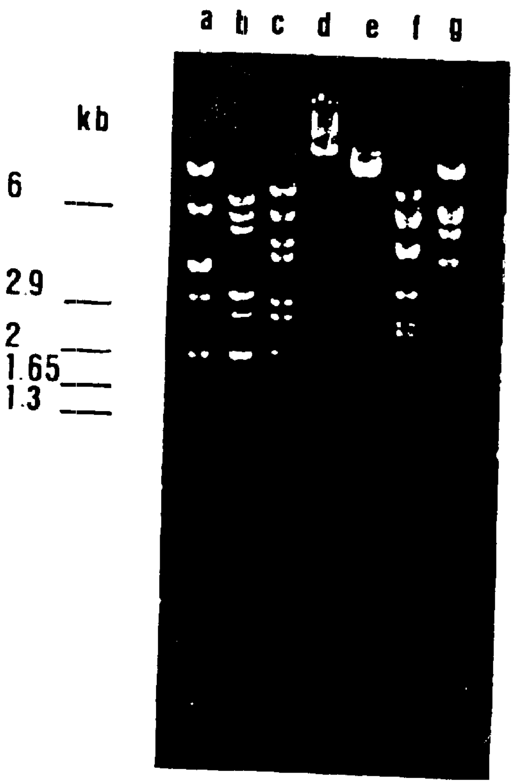

FIG. 10 represents the migration on gel of the cosmid DNA of pLA1 extracted from *E. coli* NM554 digested by BamHI (a), SmaI (b), HpaI (c), NotI (d), SspI (e), EcoRI (f) and HindIII (g).

Figure 11:

FIG. 11 illustrates the expression of the 45/47 kDa proteins in mycobacteria. The supernatants from the 7 day bacterial culture were washed and concentrated on an Amicon PM10 membrane, freeze-dried and analyzed as immuno-imprints. The proteins were revealed by polyclonal antibodies from rabbit serum diluted to 1/500.

The wells contained respectively:

(1) 0.25 μg of the purified 45/47 kDa proteins from *M. bovis* BCG, (2) 5 μg of supernatant of *M. smegmatis* $mc^2$ 155 transformed by pLA1, (3) 5 μg of supernatant from non-transformed *M. smegmatis* $mc^2$155, (4) 5 μg of *M. bovis* BCG supernatant.

Figure 12:
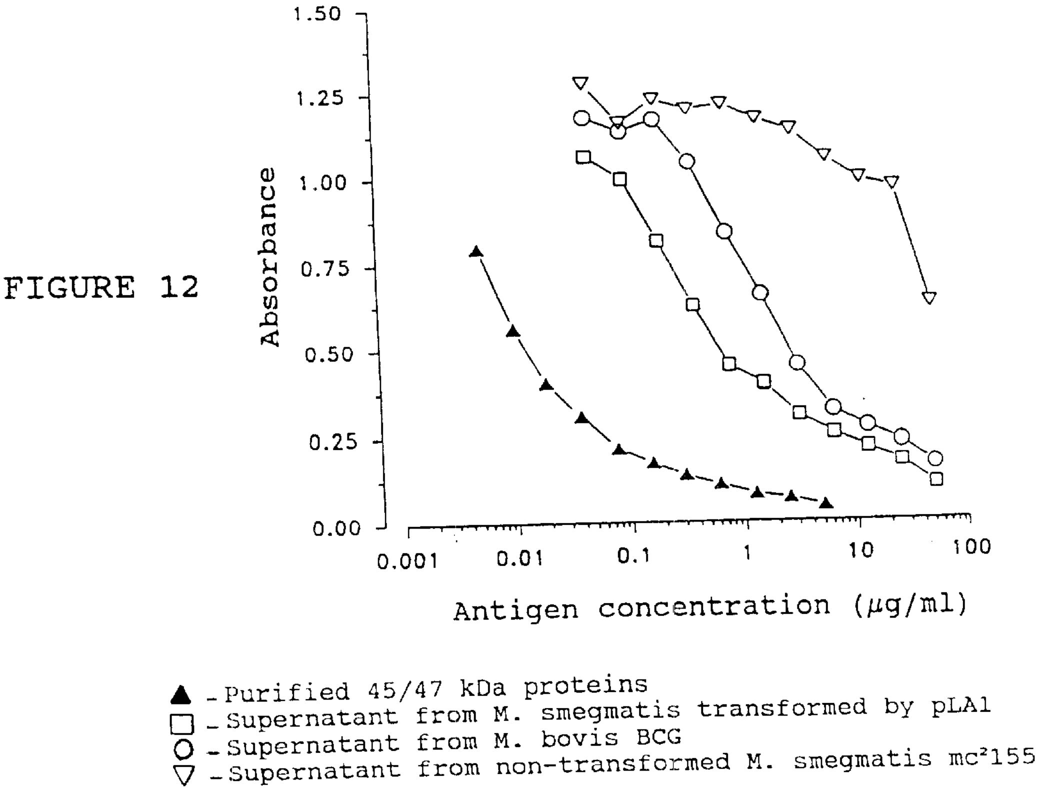

FIG. 12 illustrates the expression of the 45/47 kDa proteins in mycobacteria. The supernatants from the bacterial culture were washed and concentrated on an Amicon PM10 membrane, then freeze-dried and analysed in a competitive ELISA assay. Different concentrations of the freeze-dried supernatants were revealed with a $1/8000^{th}$ dilution of rabbit polyclonal serum, and this mixture was then transferred into wells in which the purified proteins had been fixed.

Figure 13A:
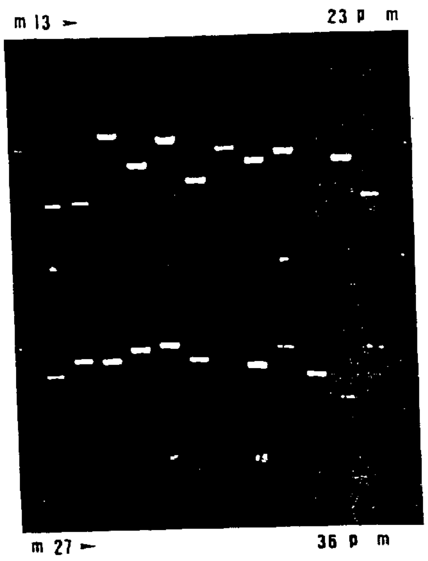
Figure 13B:
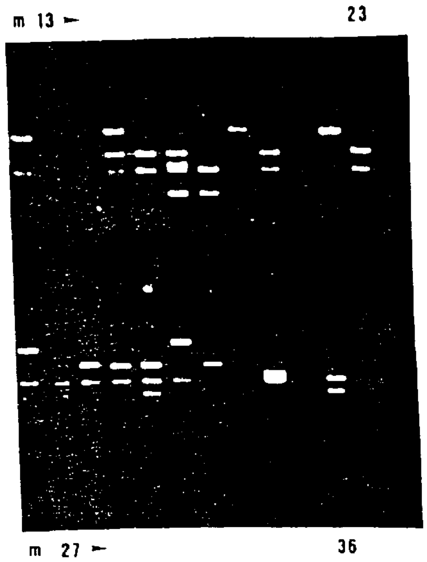

FIGS. 13A and 13B are plasmid profiles (13A) and BamHI restriction profiles (13B) of different pUC18::*M. tuberculosis* H37Rv recombinant clones, obtained by ligation of fragments from a BamH I digestion of the pLA1 cosmid in pUC18. This figure shows 21 of the 36 clones studied. The wells "p" correspond to the reference vector pUC18, and wells "m" to size markers which are fragments of the pKN plasmid cleaved by PvuII.

Figure 14:
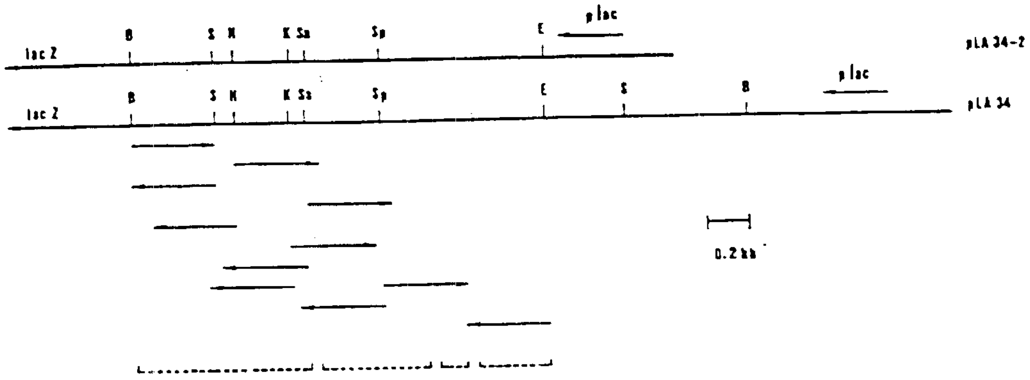

FIG. 14 is the restriction map for inserts allowing the expression of the 45/47 kDa proteins in *E. coli*. A group of clones was obtained by deletions from the Pla34 and Pla4 plasmids, containing the 3 kb insert cloned in both directions. The arrows show the direction of sequence determination from these clones through "direct" and "inverse" primers.

| | | | |
|---|---|---|---|
| B, BamH I | S, Smal | E, Ecorl | K, Kpn I |
| H. Hind III | Sa, Sal I | Sp, Sph I | |

FIG. 15 illustrates the expression of the 45/47 kDa proteins in *E. coli* The bacterial culture lysates were analyzed by immuno-imprints.

The proteins were revealed by rabbit polyclonal antibodies purified on DEAE, then absorbed on an *E. coli* lysate immobilized on a Sepharose-4B column activated by cyanogens bromide.

The wells contained respectively:

(1) 0.2 μg of the purified 45/47 kDa proteins, (2) 25 μg of lysate of *E. coli* XL-Blue transformed by Pla34-2, (3) 25 μg of lysate of *E coli* XL-Blue transformed by Pla34, (4) 25 μg of lysate of non-transformed *E. coli* XL1-Blue.

FIG. 16 illustrates the expression of the 45/47 kDa proteins in *E. coli*. The bacterial culture lysates, analyzed by a competitive ELISA assay, were used in the crude form.

FIG. 17 is a comparison of the sequence SEQ ID No2 according to the invention and the sequence of the protein from *M. leprae* (mln 431).

Figure 18:
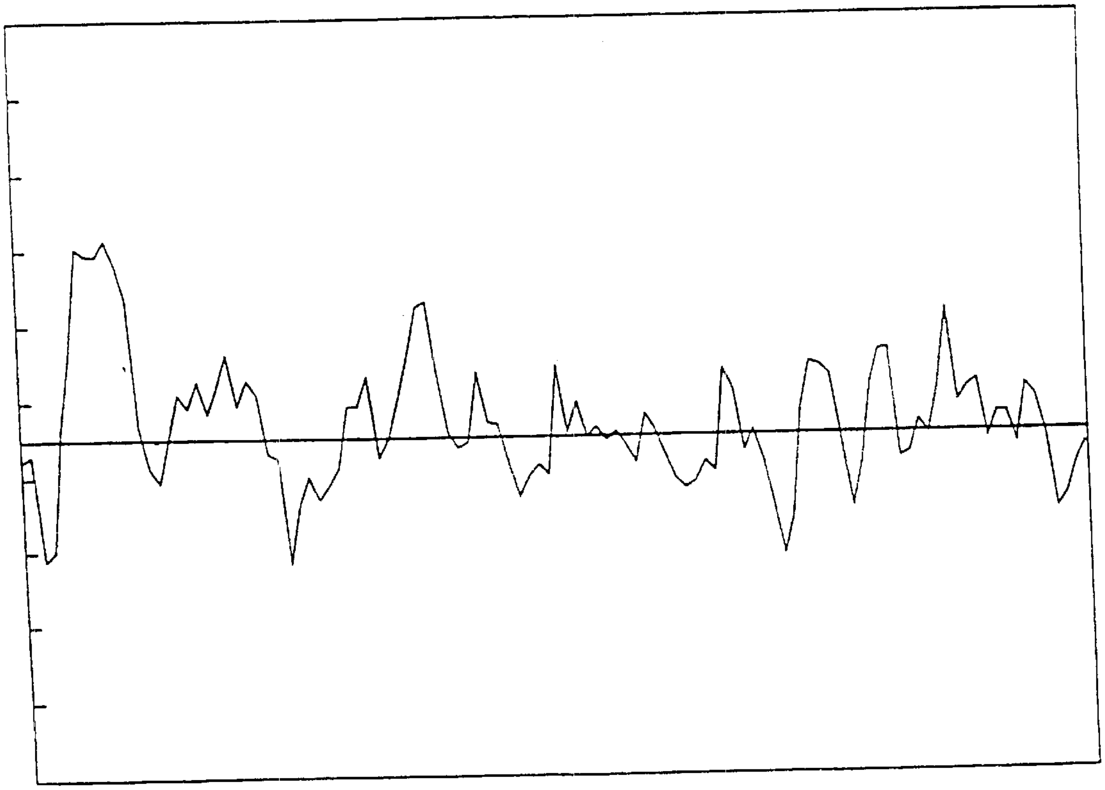

FIG. 18 is a hydrophobicity profile of the protein of sequence SEQ ID No2.

EXAMPLE 1

Purification Process for the *M. tuberculosis* Antigens

1) Obtaining the Antigens:

Cultures of *M. tuberculosis* (strain H37 Rv) were made in flasks containing 130 ml of Sauton's synthetic medium according to the conventional technique described for the culture of BCG (Gheorghiu et al., Bull. Institut Pasteur 1983, 81: 281–288). The culture medium was harvested after 20 days at 37° C., decanted and filtered (0.22 μm) at laboratory temperature. These operations were carried out in a glove box for safety reasons. The harvested and filtered culture medium was again filtered on a 0.22 μm filter under a safety hood before being used for the following operations:

After application to an Amicon (PM10) membrane under nitrogen at 2 bar and 4° C., the culture medium was washed intensively with retro-osmosed water containing 4% of butanol, then concentrated 10 to 20 times with respect to the original volume. This concentrated culture medium, containing the molecules not excluded by the Amicon PMIO membrane, was freeze-dried, weighed and stored as a powder at −20° C. The 12 g of starting material used for the purification process described below were obtained from 70 liters of culture medium.

Purification Scheme:

2) Low-pressure Ion-exchange Column:

A low-pressure preparative ion-exchange column of height 300 mm and diameter 32 mm was prepared with approximately 240 ml of Triacyl M gel (SEPRACOR). It was equilibrated with a buffered saline solution (10 mM $Na_2HPO_4/NaH_2PO_4$, pH=7, and 10 mM NaCl) containing 4% of butanol.

The concentrated and freeze-dried material prepared as in the previous stage was dissolved (in the previously described buffered saline solution ) then ultracentrifuged—for 120 minutes at 40,000 G. Only the upper portion (4/5) of the centrifuged solution was collected and placed under the control of the peristaltic pump on the ion-exchange column. A first major fraction not retained by the column was collected. A second fraction was obtained after elution of the column by a buffered saline solution (10 mM $Na_2HPO_4/NaH_2PO_4$, pH=7.5 and 1 M NaCl). After application onto an Amicon (PM 10) membrane under 2 bar pressure, each fraction was intensively washed with retro-osmosed water containing 4% of butanol, and concentrated approximately 15 times. The fraction not retained on the column contained 2.9 g of material and the majority of the molecules which were then purified in the following stages. The fraction retained on the column and then eluted by the salt solution contained approximately 1.01 g of material.

3) Gel Filtration

A high-pressure preparative Si 300 column, 3 μm, of 50×750 mm (SERVA), was equilibrated with a buffered saline solution (50 mM $Na_2HPO_4$ adjusted to pH 7.5 with $KH_2HPO_4$) containing 4% of butanol; this solution had previously been filtered on a membrane (0.22 μm). The column flow was adjusted to 1.25 ml bar per min: the maximum pressure, set at 45 bars, was not reached.

The material to be injected onto the column was prepared at a concentration of 50 mg/ml in the buffer/butanol solution. 10 ml samples were prepared and frozen at −20° C. Each 10 ml sample, refiltered after thawing and injected onto the column, contained approximately 500 mg of crude material. The optical density profiles at 240 nm are shown in FIG. 1 for a typical separation sequence. The five principal fractions selected based on the profile were concentrated at 4° C. and intensively washed on an Amicon PM10 membrane with retro-osmosed water containing 4% of butanol. Each concentrated fraction was freeze-dried, weighed and then stored at −20° C. Fraction 1 from this stage contained the principal molecules recognized by the antibodies from guinea-pigs immunized with live bacilli or by the antibodies from *tuberculosis* patients. Only this fraction was used for the following stage.

4) Ion-exchange Column:

A DEAE-TSK 5 PW preparative column 21.5×150 mm (LKB) was equilibrated with a buffered saline solution (10 mM $Na_2HPO_4/NaH_2PO_4$, pH=7.5 and 10 mM NaCl) containing 4% of butanol. The maximum pressure was below 30 bar for a 6 ml/min flow. Only the NaCl concentration was changed (1 M) for the elution buffer. A linear gradient was applied according to the scheme shown in FIG. 2 after injection of a 4 ml sample volume containing in total 100 mg of the above material. The principal fractions were collected according to the optical density profile at 240 nm. These fractions were concentrated and washed on an Amicon PM10 membrane with retro-osmosed water containing 4% of butanol, then freeze-dried. After weighing, each fraction was stored at −20° C. Only fraction 1 from this stage contained the majority of the molecules recognized by the antibodies from guinea-pigs immunized with live bacteria; these were used for the following separation stage.

5) Reversed Phase Column.

Figure 3:
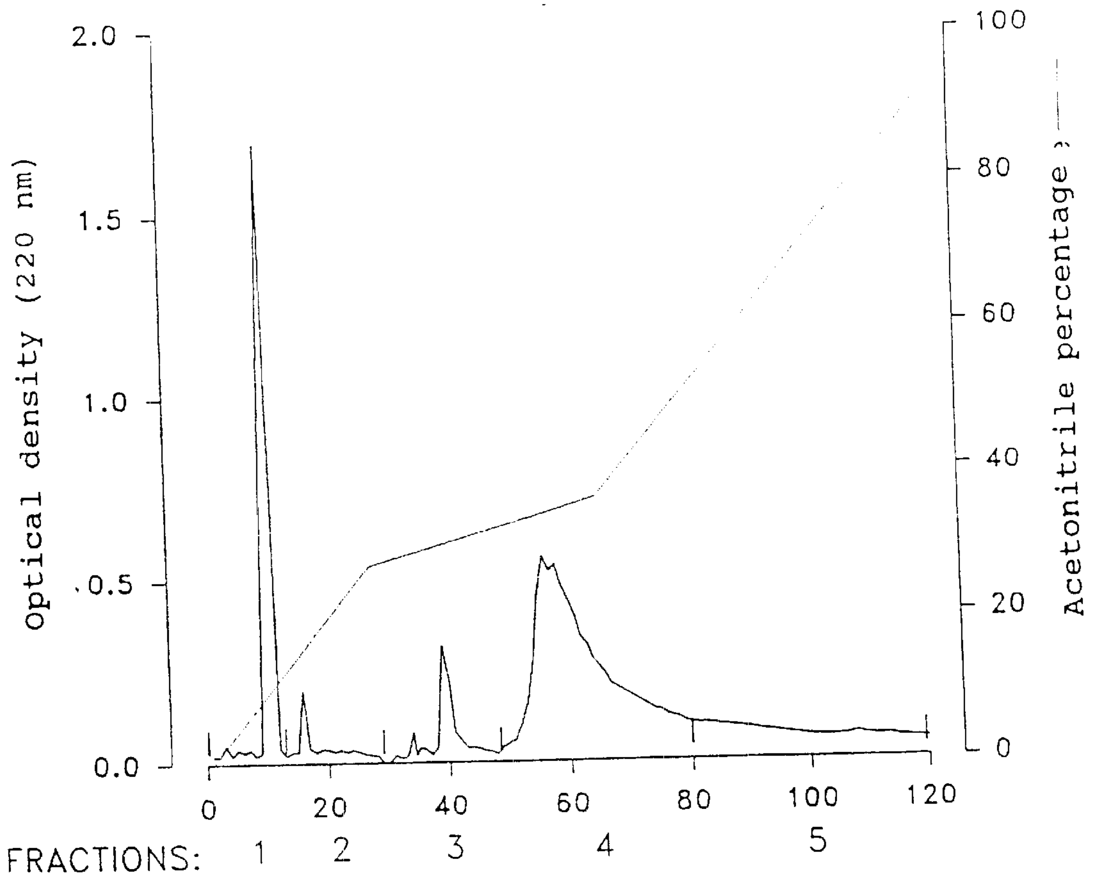
FIG. 3 shows the optical density profile at 220 nm of the reversed phase column chromatography of fraction 1 from the previous ion-exchange chromatography.

A 4.6×250 mm RP 300 $C_8$ 10 μm (Aquapore Brownlee lab.) column was equilibrated with an ammonium acetate buffer (20 mM $NH_4COOCH_3$) filtered at 0.22 μm with a flow of 2 ml/min under a maximum pressure of 115 bar. The elution buffer containing 90% of acetonitrile was applied according to the profile shown in FIG. 3 after injection of a 10 mg sample in a 1 ml volume. The optical density profile at 220 nm enabled the separation of five major fractions which were concentrated by vacuum evaporation at 40° C., then freeze-dried.

6) Immunodetection of the Antigens:

10% polyacrylamide 0.1% SDS denaturing gels were prepared according to the conventional technique of Laemmli (Nature, 1970, 277: 680–685). Samples containing between 10 and 2 μg of material, according to the purification stage, were applied in a buffer containing 5% of mercaptoethanol, 3% of SDS and a trace of bromophenol blue in a 10 μl volume in each track of the gel. After electrophoresis to the limit of migration of the blue, the molecules present in the samples were transferred on a sheet of PVDF (Millipore) by the application of a moderate electric field overnight [Harlow and Lane, Antibodies, A Laboratory Manual, Cold Spring Harbor Laboratory (Publishers), 1988].

A coloration of the PVDF sheet by a solution of Coomasie blue for less than a minute, followed by a decoloration, permitted identification of the molecular weight markers, whose shape was outlined with a pencil mark.

After total decoloration, the sheet was washed for 30 min at laboratory temperature with PBS+Triton X100 3%, then 3 times for 5 min with PBS alone. The sheet was then saturated with PBS containing 5% of powdered skimmed milk for 1 h at 37° C., then washed three times with pbs+Tween 20 (0.2%).

An incubation was carried out with the antiserums diluted to $1/20^{th}$ in the PBS+Tween 20 buffer (0.2%)+powdered milk (5%) for 1 h 30 at 37° C. with periodic agitation. Three further washings with PBS+Tween were then carried out before incubation with the anti-immunoglobulin antibodies marked with alkaline phosphatase. The human and guinea-pig anti-immunoglobulin antibodies , marked with phosphatase (Biosys), were used at a final dilution of 1/2500 in PBS+Tween 20 (0.2%)+milk (5%). After incubation for 1 h 30 min at 37° C., the PVDF sheets were washed three times with PBS+Tween, then incubated at laboratory temperature for 5 to 10 min in the revealing buffer containing BCIP and NBT (Harlow and Lane, cited above). The reaction was stopped and after drying the sheets themselves were photographed.

7) Amino Acid Composition:

An analysis of the total amino acid composition was carried out for each chromatographic fraction in the Institut Pasteur Organic Chemistry Department. A Beckmann LS 6300 analyzer was used.

The total composition expressed as amino acid frequency of the 45–47 kD proteins was as follows:

ASN/ASP: 10.4%, THR: 5.7%; SER: 5.6%; GLN/GLU: 6.3%; GLY:7.1%; ALA: 19.3%; VAL: 6.2%; ILE: 2.2%; LEU: 4.4%; TYR: 2.2%; PHE: 2.4%; LYS: 2.7%; ARG: 2.7%; PRO: 20.9%.

EXAMPLE 2

Determination of the Immunological Specificity of the Proteins and Protein Fractions of *M. tuberculosis* and Isolation of the Antigens Recognized by the Antibodies From Guinea-pigs Immunized With Live Bacilli Groups of 12 to 15 guinea-pigs (Hartley females of 250 to 300 g at the beginning of the experiment) received either live mycobacteria ($2\times10^7$ viable units of BCG in two intradermic injections in 0.1 ml of saline solution), or 2 mg of heat-killed (120° C., 30 min) mycobacteria from the same strain intramuscularly in 0.5 ml of a saline solution emulsion in incomplete Freund's adjuvant (1/1). Serum samples from different groups of guinea-pigs were taken 7 to 12 months after immunization, filtered (0.22 μm), then separated into small volumes which were frozen and stored at −20° C. Tests of several groups of antiserums were carried out (5 after immunization with live bacteria and 6 after immunization with killed bacteria). The results reported were obtained with a group of serums representative of each type of immunization; the differences between groups were minimal for the same immunization method.

1) Separation Stage On a Low-pressure Ion Exchange Column.

The culture medium (washed and concentrated on an Amicon PM10 membrane then freeze-dried) was ultracentrifuged then loaded onto a low-pressure ion-exchange column. Two fractions were obtained, one not retained by the column and the other eluted by a high-molarity buffered solution, and were washed and concentrated on an Amicon PM10 membrane, then freeze-dried.

Each fraction (10 μg) was placed on an SDS gel track and then, after the electrophoresis sequence, transfer on a PVDF membrane and immunodetection, the fractions containing the predominant molecules reacting with the different serums were identified.

Figures 4A, 4B, 4C, 4D, 4E:
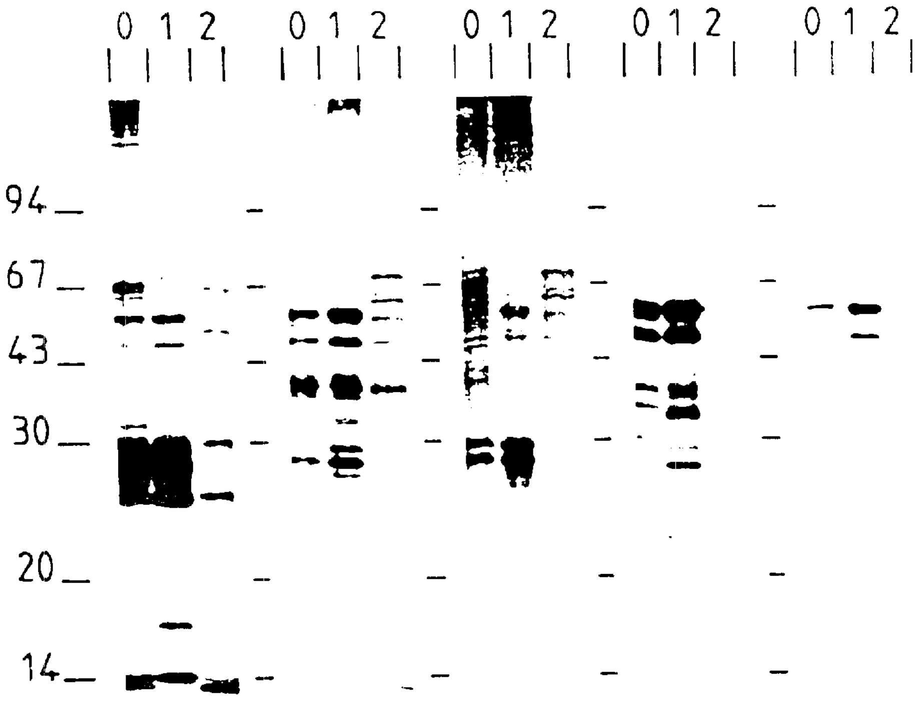
FIGS. 4A to 4E are photographs of PVDF membranes revealed by respectively.
Figure 5C:
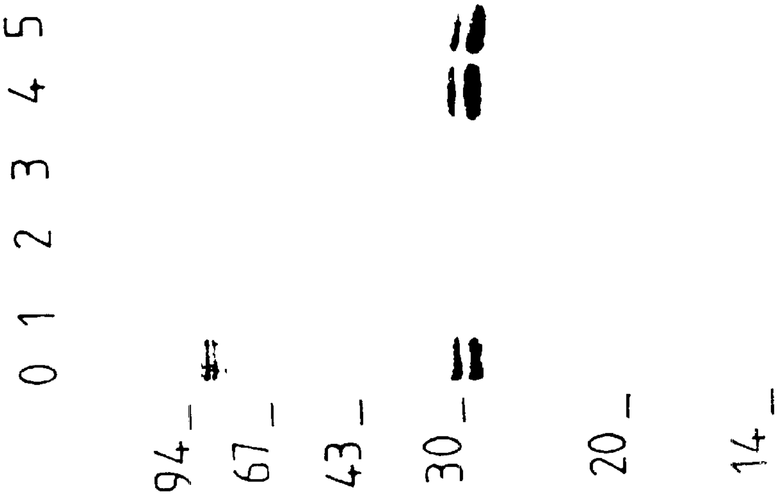
Figure 5B:
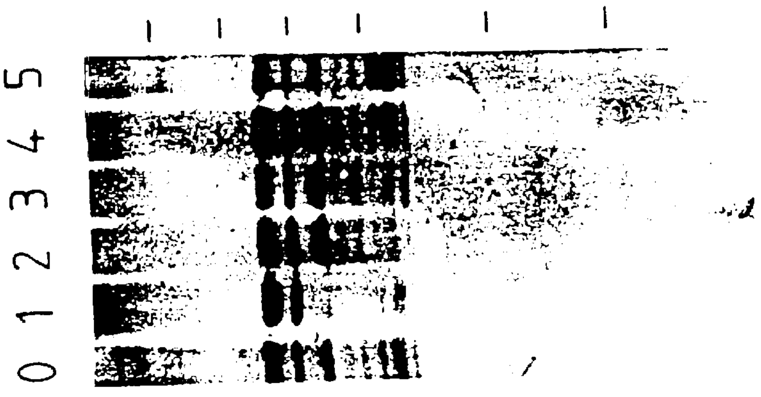
Figure 5A:
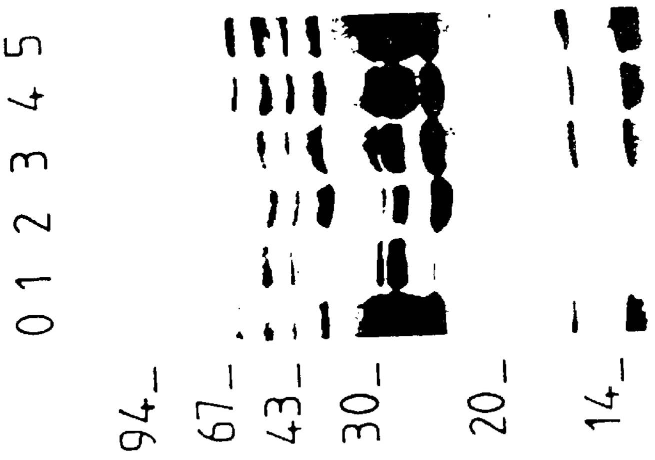
Figure 5D:
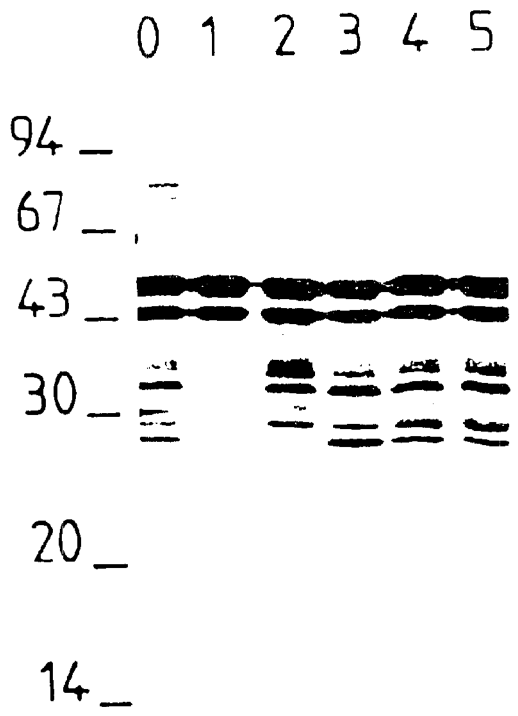
Figure 5E:
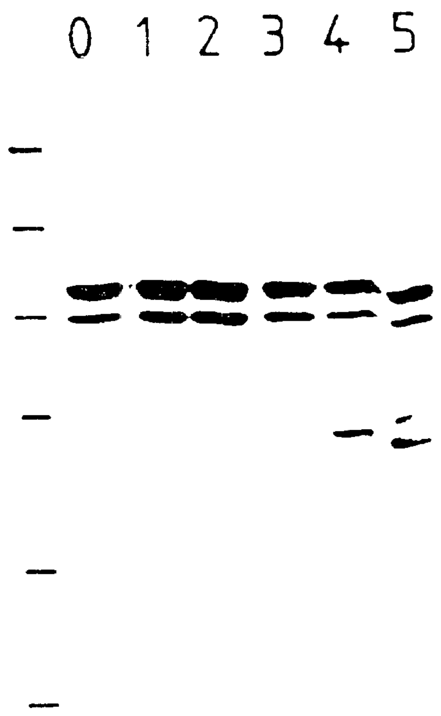

FIG. 4 shows the immuno-imprints of identical gels revealed with a colorant for the transferred proteins (Aurodye-Amersham) (4A) or serums from guinea-pigs immunized with live (4B) or dead (4C) bacilli. The immuno-imprints 4D and 4F were revealed respectively with a rabbit serum directed against molecules identical to BCG (Infection and Immunity, 1993, 61, 742–750) and the supernatant of the I-1081 hybridoma producing of a monoclonal antibody, deposited with the Collection Nationale de Cultures de Microorganisms (CNCM) at the Institut Pasteur. Only the fraction not retained on the column contained the 45–47 kDa molecules recognized by the serums from guinea-pigs immunized with the live or dead bacilli or recognized by the supernatant of the hybridoma described above.

2) Molecular Filtration Stage on Si 300

The non-retained fraction from the previous stages was injected in a sample volume of 10 ml containing 500 mg of material onto the Si 300 column. Fractions 1 to 5 were separated according to the profile shown in FIG. 1, the products from successive injections were combined together, then washed, concentrated and freeze-dried.

Each fraction (10 μg) was placed on an SDS gel track; then, after the electrophoresis sequence, transfer on PVDF membrane and immunodetection, the fractions containing the predominant of the proteins reacting with the different serums were identified.

FIG. 5 shows the immuno-imprints of identical gels revealed after protein coloration (Aurodye-Amersham) or with the serums from guinea-pigs immunized with live (5B) or dead (5C) bacilli. The immuno-imprints 5D and 5E were revealed with respectively a rabbit serum directed against these molecules purified from BCG and with the I-1081 monoclonal antibody.

Two 45 and 47 kD antigens present in fraction 1 were mainly recognized by the antibodies from animals immunized with live bacilli or with the polyclonal rabbit serum or with the monoclonal antibody. This fraction was selected for the second purification stage.

3) Ion Exchange Stage.

Figure 2:
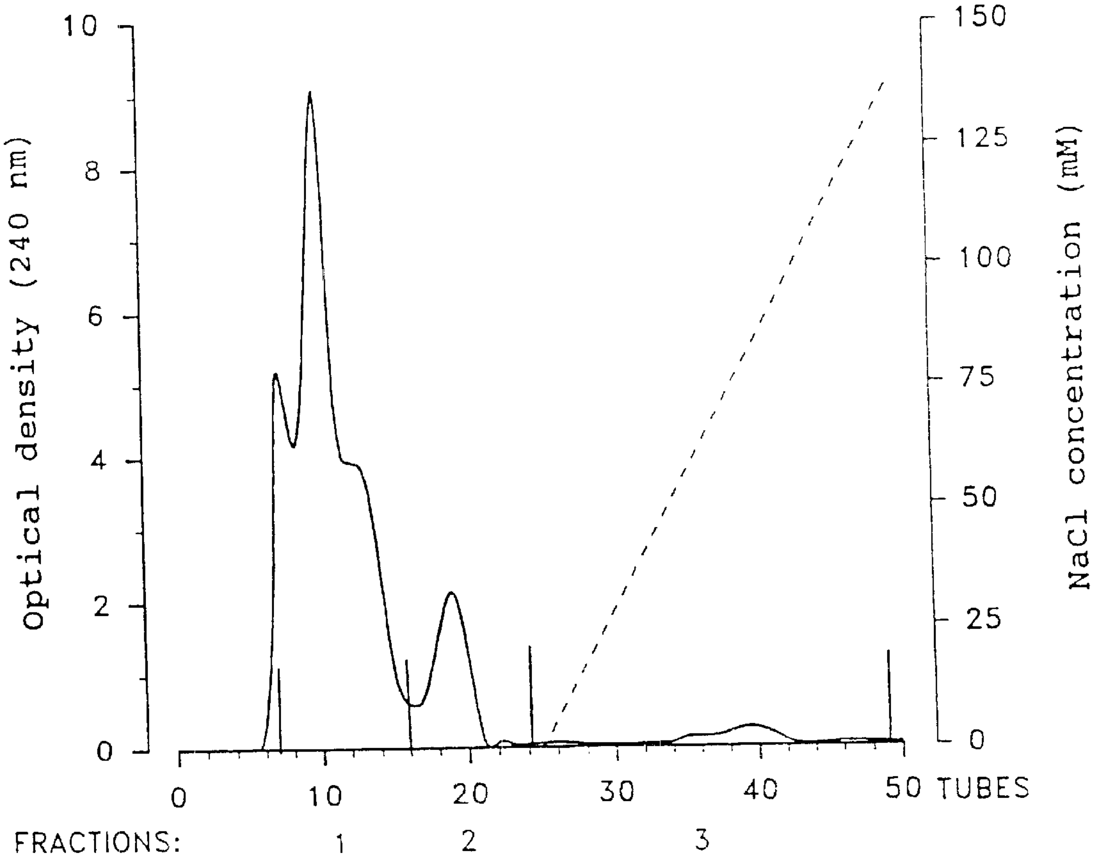
FIG. 2 shows the optical density profile at 220 nm of the separation on a high-pressure ion-exchange column (DEAE) of molecules originating from fraction 1 obtained from the previous molecular filtration.

A 100 mg sample of the above fraction was loaded onto a DEAE-TSK preparative column and eluted by an NaCl gradient. The 220 nm profile of the molecules eluted defined three principal fractions (FIG. 2). After collection together, each fraction obtained by the successive injections of material was washed, concentrated and freeze-dried.

Figures 6A, 6B, 6C, 6D, 6E:
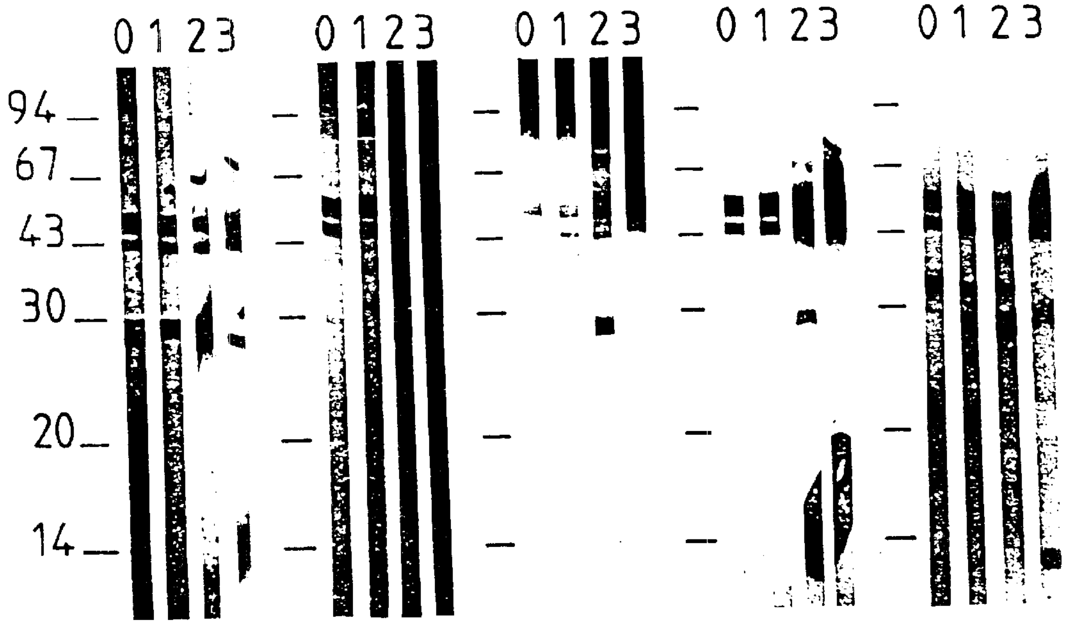
Figure 7A:
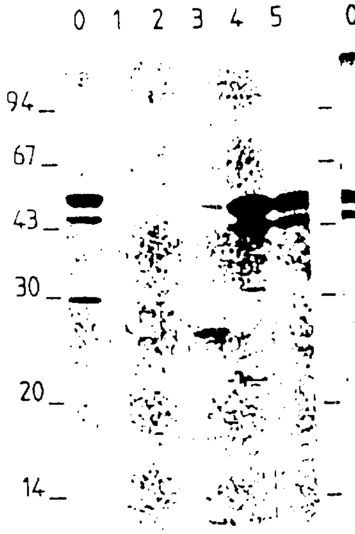
Figure 7B:
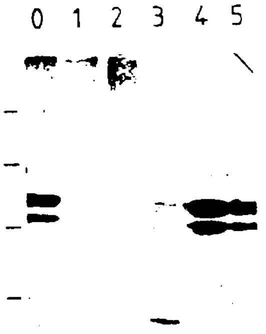
Figure 7C:
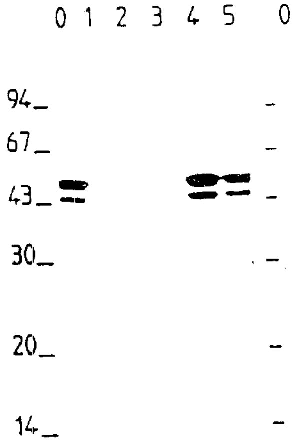
Figure 7D:
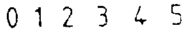

After electrophoresis on SDS gel of 5 μg of each of the above fractions, the immuno-imprints on PVDF sheets were revealed by the protein colorant (aurodye) (FIG. 6A), by the serums from guinea-pigs immunized with live (FIG. 6B) or dead (FIG. 6C) bacilli, rabbit serum (FIG. 6D) or monoclonal antibody (FIG. 6E). The fraction 1-DEAE contained only a few antigens recognized by the antibodies from animals immunized with dead bacilli. On the other hand, this same fraction 1-DEAE contained a doublet at 45/47 kD strongly recognized by the antibodies from guinea-pigs immunized with live bacilli, as well as the rabbit serum and the monoclonal antibody. This fraction 1-DEAE was selected for the following purification stage.

4) Reversed-phase Column Stage:

A 10 μm RP 300 column, equilibrated with the ammonium acetate buffer (20 mM), received a 1 ml sample containing a maximum of 5 to 10 mg of the above fraction 1-DEAE. Elution with an acetonitrile gradient of 0 to 90% according to the scheme of FIG. 3 allowed recovery of five principal fractions. These fractions were concentrated by vacuum evaporation at 40° to eliminate the majority of the acetonitrile, then freeze-dried.

Fraction 4 (30–50% acetonitrile gradient) contained the majority of the molecules recognized by the antibodies from animals immunized with live bacilli or by the antibodies present in the rabbit serum or by the monoclonal antibody, and mainly these molecules after coloration of the proteins by Aurodye (FIG. 6).

EXAMPLE 3

Cloning and Expression of the 45/47 kD Proteins From *Mycobacterium tuberculosis* in *Mycobacterium smegmatis* and *Escherichia coli*

1) Materials and Methods 1.1 Bacterial Strains and Growth Conditions, Preparation of Supernatants and Bacterial Extracts.

*M. bovis* BCG (strain $1173P_2$) was cultivated in Sauton's synthetic medium for 7 days at 37° C., and the supematant was then filtered on a 0.22 μm membrane. These supernatants were then stored crude in the presence of 4% butanol or concentrated on an Amicon-PM membrane and freeze-dried.

*M. smegmatis* $mc^2$ 155 (Snapper et al., 1990, Molecular Microbiol., 4, 1911–1919) was cultivated in an 7H9+OADC liquid medium for 7 days at 37° C. Each *M. smegmatis* $mc^2$ 155 clone transformed by the cosmids from the pYUB18:*M. tuberculosis* library was cultivated in the presence of kanamycin at 25 mg/ml. The cultures were then centrifuged for 15 min at 5000 rpm, and the supernatants from the culture were separated and stored at 4° C. in the presence of 4% butanol. These preparations were used for the ELISA assays in which the composition of the medium did not interfere. When the supernatants from the clone culture were analysed on SDS-PAGE gel, these were cultivated in Sauton's synthetic medium for 7 days at 37° C., the culture supernatants were filtered on a 0.22 μm membrane, then concentrated on an Amicon-PM10 membrane and freeze-dried.

The *E.coli* NM554 and XL 1-Blue strains were cultivated in solid or liquid Luria-Bertani (LB) medium at 37° C. The *E.coli* XL 1-Blue clones, transformed by the pUC18 plasmid, were cultivated in the presence of 25μg/l of ampicillin.

The bacterial culture lysates of *E.coli* XL1-Blue and of each clone transformed by the recombinant pUC18*: M. tuberculosis* plasmids were prepared by a rapid freezing/thawing series at −70° C. and +60° C. of bacteria obtained after culture for one night (16 h). The lysates were centrifuged, and the supernatants separated and stored at −20° C. An analysis of the proteins from these preparations was carried out by the BCA technique (Pierce).

i.2 Cloning Vectors

The gene library from *M. tuberculosis* used (Jacobs et al., 1991, cited above) was produced by electroporation in *M. smegmatis* $mc^2$ 155 by Steward Cole. The applicant had 400 recombinant clones available.

The library Was created in a cosmid, shuttle vector pYUB18. This latter was derived from the pYUB12 plasmid (Snapper et al., Proc. Natl. Acad. Sci., USA, 1988, 85:6987–6991) in which the Cos sequence of the lambda bacteriophage had been inserted, enabling an amplification and good retention of the recombinant cosmids in the library in the form of phage lysates. This library had been created in the following way: the genomic DNA from *M. tuberculosis* strain H37Rv had been partially digested by enzyme Sau 3a, under conditions allowing a maximum of 35 kb to 45 kb fragments to be obtained. These fragments were purified then ligated in pYUB18, digested by the restriction endonuclease BamHI and dephosphorylated.

The pUC18 μlasmid vector (Yanisch-Perron et al., Gene, 1985, 33: 103–119) was used for the subcloning in *E. coli* XL-Blue. This multicopy plasmid carries a DNA fragment derived from the lac operon of *E. coli* which codes for a terminal amino-fragment of beta-galactosidases. This fragment is inducible by isopropyl beta-D-thiogalactopyranoside (IPTG) and is able to establish alpha-complementation with the defective beta-galactosidase form coded by the *E. coli* XL1-Blue host strain. The insertion of foreign DNA thus induces an abolition of alpha-complementation. The recombinant plasmids can be identified when they are transformed in the host strain by the white colour of the colonies, compared with the blue colour of the colonies when the bacteria have been transformed by the pUC18 plasmid. This screening was carried out in the presence of IPTG and X-Gal enzyme substrate.

1.3 Molecular Biology Techniques 1.3.1 Extraction of *M. Smegmatis* $mc^2$ 155 Cosmids The extractions of recombinant pYUB18:*M. tuberculosis* cosmids were carried by use of the alkaline lysis technique adapted for *M. smegmatis* (Jacobs et al., 1991, cited above) with some modifications. The bacteria were collected on the fifth day of culture (end of the exponential phase), and centrifuged for 10 min at 5000 rpm. The bacterial residue (3 ml) was resuspended in 5 ml of solution A (50 mM glucose, 25 mM tris HCl pH 8, 10 mM EDTA, lysozyme 10 mg/ml) and incubated at 37° C. for 20 minutes. Two volumes (10 ml) of solution B (0.2 N NaOH, 1% SDS) were then added and mixed by inversion. The mixture was incubated for 30 minutes at 65° C., then 15 minutes at 4° C. Finally, 1.5 volumes (7.5 ml) of solution C (5 mM potassium acetate, acetic acid 11.5%) was added and mixed by inversion. The mixture was incubated for 30 minutes at 4° C. The preparation was then centrifuged for 15 minutes at 13000 rpm at 4° C., the supernatant recovered, measured and treated with the same volume of 50/50 phenol/chloroform.

After extraction, the tube was centrifuged at 4000 rpm for 10 minutes. The aqueous phase was transferred into a clean tube and treated with twice the volume of ethanol stored at −20° C. After inversion, this was kept for at least 1 hour at −20 C., then centrifuged for 20 minutes at 12000 rpm. The residue was finally washed with one volume of 70% ethanol stored at −20° C. and dried in a Speed-Vac for 5 minutes. The dry residue was taken up in 500 μl of sterile water and stored at −20° C.

1.3.2 Extraction and Purification of *E. Coli* Plasmids

The rapid extractions of pYUB18 cosmids and pUC18 recombinant plasmids were carried out by the alkaline lysis technique (Birnboim et al., Nucleic Acids Res., 1979, 7:1513).

The relevant cosmids and recombinant plasmids were purified after an alkaline lysis stage by ultracentrifugation on a cesium chloride gradient in the presence of ethidium bromide (Maniatis et al., Cold Spring Harbour, N.Y.: Cold Spring Harbour Laboratory Press, 1982).

1.3.3 Transformation Techniques

Chemical Method with Calcium Chloride

This conventional technique was used for transforming *E. coli* XL1-Blue by pUC18 recombinant plasmids. The competent bacteria were first prepared: 20 ml of 2Yt medium were sown with a preculture for one night at 1/100. The bacteria were subjected to culture under agitation for 2 hours at 37° C. until OD=0.6, then centrifuged for 10 minutes at 4000 rpm at 4° C. The residue was taken up in 8 ml of 100 mM $CaCl_2$, kept for 15 minutes in melting ice, then centrifuged again for 10 minutes at 4000 rpm at 4° C. The residue was finally taken up in 1.6 ml of 100 mM $CaCl_2$, kept in melting ice for 30 min.

The competent bacteria thus prepared were freshly used for transformations or could be stored for several days at 4° C. At the moment of transformation 200 μl of competent bacteria were mixed with 2 μl of DNA. The mixture was stored for 45 minutes in melting ice, then subjected to thermal shock for 2 minutes at 42° C. 800 μl of 2YT medium were added, then the preparation was incubated for one hour at 37 with agitation, then spread onto ML-ampicillin dishes at 50 μl to 200 μl per dish. The next day the colonies were counted and the efficiency of the transformation was calculated.

Physical Electroporation Method

This technique was used for transforming *E. coli* by large vectors strain NM554 of *E. coli* was electropored by recombinant pYUB18 cosmids of size greater than 50 kb. The competent bacteria were freshly prepared 200 ml of 2YT medium were sown with a preculture at a dilution of 1/100 for one night; the bacteria were cultivated for 3 hours at 37° C., then centrifuged at 6000 rpm for 10 minutes. The residue was taken up in 10 ml of sterile water at 4° C., then in 190 ml of sterile water at 4° C.

The bacteria were again centrifuged at 6000 rmp for 10 minutes and rewashed with 10 ml of sterile water at 4° C. Finally the residue was taken up in 400 μl of 10% glycerol.

The electroporation was carried out on a Bio-Rad Gene Pulser. 100 μl of bacteria were mixed with 1 to 4 μl of DNA in a 0.4 mm cell. The mixture was subjected to electrical shock (2500 volts, 25 μF), then 1 ml of 2YT medium was rapidly added to the cell. The whole was transferred into a tube and incubated for 1 hour at 37° C. with agitation. After incubation the culture was spread onto ML-ampicillin dishes at 50 μl to 200 μl per dish. The next day the colonies were counted and the efficiency of the transformation was calculated.

1.3.4 Cloning of Fragments From Enzymatic Digestion

The DNA to be cloned was digested by a BamHI restriction endonuclease. The pUC18 plasmid was digested in the same way. The fragments resulting from the required pYUB18 recombinant cosmid were ligated in the plasmid vector by the activity of the T4 DNA ligase enzyme (Amersham). Ligation was carried out in a 20 μl volume at 16° C. overnight. The whole of the ligation mixture was used for transformation in *E. coli* XL1-Blue. After phenotypic expression, all the bacteria were spread on ML-ampicillin plates at 25 μg/ml, IPTG, X-Gal. The recombinant clones not permitting alpha-complementation were located from the white colour of these colonies.

The recombinant clones were studied after purification by cloning. The plasmid DNA was extracted by alkaline lysis then analyzed on 0.8% agarose gel before or after digestion with restriction endonuclease BamHI.

1.3.5 Production of a Restriction Map

The pLA34 and pLA4 recombinant plasmids, containing a 3 kb BamHI-BamHI insert cloned in both directions, were digested by the different restriction endonucleases having a site in the pUC18 multisite linker (polylinker). Single and double digestions were carried out by use of the restriction endonucleases BamHI, HindIII, SphI, XbaI, SalI, KpnI EcorI and SmaI, then analyzed on 0.8% agarose gel. After coloration of the DNA with ethidium bromide the size of the different fragments was determined as a function of their migration distance compared with the markers (an internal laboratory standard, pKN plasmid digested by PvuII).

1.4 Methods of Protein Detection 1.4.1 ELISA Technique

A competitive ELISA test was used for measuring the concentration of the 45/47 kDa proteins in the different preparations obtained from bacterial cultures, by use of a polyclonal serum (Romain et al., 1993, cited above).

This polyclonal rabbit serum was obtained against the 45/47 proteins by a conventional immunization technique: injection of 50 μg of purified proteins in incomplete Freund's adjuvant and of 25 μg one month later.

The wells of a first microplate were covered either by purified proteins in solution at a concentration of 1 μg/ml in carbonate buffer or by a 15 day *Mycobacterium bovis* BCG supernatant at a concentration of 10 μg/ml. The antigen fixation was carried out for one hour at 37° C., and the microplate was then washed five times with PBS. In a second incubation the wells were saturated with a solution of PBS, 0.5% gelatin, 4% butanol for one hour at 37° C. The microplate was then washed 5 times with PBS-Tween 0.1%.

The test was carried out as follows:

Incubation in a second microplate of 50 μl of the supernatant to be analyzed at different dilutions (pure, 1/2, 1/4, 1/8, etc) in PBS-Tween 0.1%, 0.25% gelatin, 4% butanol and of 50 μl of rabbit serum prepared at a dilution of 1/4000 in PBS-Tween 0.1%, 0.25% gelatin, 4% butanol, for one hour at 37° C., then transfer of the mixture onto the first microplate and incubation for one hour at 37° C. The microplate was then washed 10 times with 0.1% PBS-Tween. Finally and anti IgG H+L anti-rabbit conjugated antibody (Biosys), marked with alkaline phosphatase, prepared at a dilution of 1/4000 in PBS-Tween 0.1%, 0.25% gelatin, 4% butanol, was incubated for one hour at 37° C. The microplate was washed 10 times with PBS-Tween 0.1%.

The enzyme substrate, para-nitrophenyl phosphate (pNPP) was finally incubated at a concentration of 40 mg/24 ml in a $NaHCO_3$, $MgCl_2$, pH 9.6 buffer for one hour or overnight. The OD were read at 414 nm and 690 nm on a Titerteck Twinreader.

1.4.2 Immuno-imprint Technique

The conventional gel-electrophoresis technique on denaturing SDS-PAGE gel was used (Laemmli, Nature, 1970, 277:680–685), followed by an electrotransfer on a PVDF membrane (Towbin et al., Proc. Natl. Acad. Sci. USA, 1979, 76:4350–4354 ; Pluskal et al., Biotechniques, 1986, 4: 272–283).

The samples analyzed on gel were measured quantitatively; in μg of lyophilizate for the *M. smegmatis* supernatants (5 μg were applied) and in μg of proteins for the *E. coli* lysates (25 μg were applied).

The purified *M. bovis* BCG proteins were placed on the gel at a concentration of 0.25 μg of protein per track.

The proteins transferred on the membrane were revealed by rabbit polyclonal serum at a dilution of $1/500^{th}$ for the proteins expressed in the mycobacteria.

In order to reveal the recombinant proteins in *E. coli*, these polyclonal antibodies were purified on a DEAE ($Trisacryl^D$) column, and the immunoglobulins obtained then absorbed on an *E. coli* lysate immobilized on a Sepharose-4B column activated by cyanogen bromide (Pharmacia) (Maniatis et al., 1982). The non-retained antibodies were stored in a pool at 4° C. then used for revealing the proteins transferred on the membrane at a dilution of $1/100^{th}$.

An anti-Ig H+L conjugate (Bio-Sys), species-specific marked by alkaline phosphatase, was used for revealing the above antibodies at a dilution of 1/3000. Finally, the alkaline phosphatase activity was revealed by two artificial chromogenic substrates: tetrazolium blue and 5-bromo-4-chloro-3-indolyl phosphate.

1.5 DNA Sequencing

The nucleotide sequencing was carried out by use of a group of clones obtained by different deletions from the two clones pLA34 and pLA4. The deletions were selected according to the restriction map established.

The sequencing was performed from double-stranded plasmid DNA matrices. Sanger's technique was applied by use of a T7 Sequencing kit (Pharmacia and $^{35}S$ ATP.

The sequence was obtained by use of different deleted clones and universal primers (Direct and Reverse Primers) of the pUC18 plasmid, then synthetic oligonucleotides.

The sequences were established on the two complentary strands.

The compression zones resulting from the high percentage of GC in the genomic DNA of *M. tuberculosis* (65%) were sequenced with the aid of a T7 Deaza G/A Sequencing kit (Pharmacia) containing 7-Deaza dGTP, a chemical analogue of dGTP.

1.6 Sequence Analysis:

The comparisons and assemblies of the contiguous sequences obtained were carried out with the help of the STADEN program on Unix. The sequence homologies searches for among the sequences of the EMBL and GenBank data banks were made by use of the FASTA and T-FASTA programs of GCG.

2) Results 2.1 Cloning and Expression of the 45/47 kDa Proteins From *M. tuberculosis* in *M. smegmatis*

2.1.1 Screening of a Gene Library for Expression of *M. Tuberculosis* In *M. Smegmatis*

The gene library used (Jacobs et al., 1991, cited above) was created by cloning the 40 kb fragments resulting from a partial genome digestion by the restriction endonuclease Sau 3a in the pYUB18 cosmid vector. The size of the genome, estimated by pulsed field electrophoresis at 4200 kb, is thus contained in approximately 100 to 150 clones.

A competitive ELISA test was used to determine the proteins in liquid medium (Romain et al., 1993, cited above). It enabled the detection and definition of the quantity of the 45/47 kDa proteins in the supernatant from 7 day cultures of *M. bovis* BCG (FIG. 8).

This test has the following advantages: good sensitivity, that is the ability to detect a quantity of the order of 1 ng/ml of proteins in liquid medium by use of a polyclonal serum diluted to $1/8000^{th}$ (Romain et al., 1993, cited above) and ease of operation for rapidly screening a series of samples.

A series of 400 pYUB18::*M. tuberculosis* H37Rv recombinant clones, eletropored in *M. smegmatis*, was screened.

For this, the different clones were cultivated for 7 days in 7H9+OADC medium. The recombinant proteins were searched for in the test by analyzing the supernatants obtained after centrifuging the cultures.

Three clones were found which were able to express the proteins recognized by the specific monoclonal antibodies of the *M. bovis* BCG 45/47 kDa proteins (FIG. 8). During this first screening he wells of the microtitration plates were covered by a supernatant of *M. bovis* BCG culture in which the 45/47 kDa proteins had been evaluated at 2% of the total mass. The three clones selected were confirmed in a second experiment in which the wells of the microtitration plates were covered by the purified 45/47 kDa proteins.

2.1.2 Genetic Analysis of the Selected Recombinant Plasmids

In order to study the different cosmids selected, these were electropored in *E. coli* NM554 after extraction of the *M. smegmatis* DNA by modified alkaline lysis. Mycobacterial extrachrosomal DNA is in fact difficult to obtain owing on the one hand to the complexity of the cell wall, which is difficult to lyse, and to the low number of vector copies which has been determined as 3 to 10 on average per bacterium. The three clones transformed in *E. coli* NM554 were isolated on ML-kanamycin dishes, and the cosmid DNA, extracted by alkaline lysis, was analyzed on 0.8% agarose gel.

The three clones had a DNA of size greater than 50 kb. Digestion by restriction endonuclease BamHI was carried out to differentiate the profiles of these three selected cosmids. These were revealed to be identical (FIG. 9). The profiles showed a 12 kb band corresponding to the pYUB18 vector, then a series of bands of lower molecular weight corresponding to the cloned DNA fragment (approximately 40 kb). Taking account of the number of bands obtained and their location on the gel, it could be considered that the cosmids isolated were identical.

Different digestions of the pLA1 cosmid alone were carried out by restriction endonucleases with more or less frequent cleavage sites for a DNA rich in G+C in order to differentiate the fragments with medium length, sufficient to contain the gene or genes for the 45/47 kDa proteins, and to carry out a sub-cloning of these (FIG. 10).

2.1.3 Expression of the 45/47 kDa Proteins from *M. tuberculosis* in *M. smegmatis*

The pLA1 cosmid containing an insert of approximately 40 kb allowed the expression of recombinant proteins in *M. smegmatis*, detected in a culture supernatant by polyclonal antibodies.

In order to determine the approximate sizes of the proteins expressed, a freeze-dried supernatant from a 7 day culture was analyzed by immuno-imprint. The recombinant proteins expressed in *M. smegmatis* had two molecular weights of 45/47 kDa apparently identical to those expressed in *M. bovis* BCG (FIG. 11).

In another experiment, the level of expression of these recombinant proteins was compared to that in *M. bovis* BCG. A measured quantity of proteins from freeze-dried supernatants was used during a determination by a competitive ELISA test. Different concentrations of lyophilized supernatants were revealed with a $1/8000^{th}$ dilution of rabbit polyclonal serum. Recombinant *M. smegmatis* allowed the expression of the proteins in quantities 5 times greater than for *M. bovis* BCG (FIG. 12).

A sub-cloning of this insert, together with an analysis of the recombinant proteins in the heterologous host (*E. coli*), was carried out in order to determine the number of genes coding for these proteins.

2.2 Cloning and Expression of the 45/47 kDa Proteins from *M. tuberculosis* in *E. coli.*

2.2.1 Sub-cloning and Expression of the 45/47 kDa Proteins in *E. Coli*

When pLA1 had been transformed in a heterologous host *E. coli* NM554, no recombinant proteins was detected in the supernatants from the bacterial cultures or lysates. In order to favour the expression of these proteins, a sub-cloning of the fragments resulting from a BamHI digestion of the cosmid was carried out in the pUC18 μplasmid (Yanisch-Perron et al., Gene, 1985, 33:103,119).

The pUC18::*M. tuberculosis* recombinant plasmids transformed in *E. coli* XL1-Blue were selected by lack of beta-galactosidase expression of the host bacteria. The plasmid DNA of each "White" clone from a series of 36 clones) was prepared by alkaline lysis and digested by restriction endonuclease BamHI.

The size of the plasmids obtained observed in agarose gel showed several profiles indicating that the recombinant plasmids were different (FIG. 13A).

The size of the cloned inserts also observed in agarose gel showed different restriction profiles (FIG. 13B). These profiles all showed a 2.8 kb fragment corresponding to the pUC18 vector and a series of fragments of different sizes corresponding to the cloned inserts.

All the digestion fragments were cloned alone, in twos or in threes, except for the 12 kb fragment which was difficult to clone because of its large size.

The 36 clones selected were screened for their ability to induce the expression of recombinant proteins in *E. coil* XL1-Blue. This experiment was carried out in the same competitive ELISA test as before.

No recombinant protein was detected in the bacterial culture supernatants. On the other hand recombinant proteins were detected in the bacterial lysates of clones containing at least one 3 kb insert.

The level of expression of the proteins measured in the test seemed to be influenced by the size of the plasmids. Among the 36 clones studied, 2 clones were found to allow expression, pLA34 and pLA35, containing 3 kb and 7 kb inserts respectively. This was greatest for pLA34 as shown by the results in table 1 (see below).

2.2.2. Restriction Map of the pLA34 and pLA34-2 Clones

A restriction map for the pLA34 μlasmid was established, identifying different cleavage sites for current restriction endonucleases, present in the multisite linker (polylinker) of pUC18 (FIG. 14). A single restriction site EcoRI separated the 3 kb insert into two fragments of 2 kb and 1 kb.

The pLA34-2 clone having a 2 kb BamHI-EcoRI insert was produced from the above clone by deletion. This also allowed expression of recombinant proteins in the bacterial lysates (FIG. 15).

Immuno-imprint analysis of the bacterial lysates showed proteins with two molecular weights of 45 and 47 kDa, apparently identical to the native proteins expressed in *M. bovis* BCG (FIG. 16).

2.2.3 Analysis of the Nucleotide Sequence Coding for the 45/47 kDa Proteins of *M. tuberculosis* H37Rv:

The complete nucleotide sequence of the gene coding for the 45/47 kDa proteins, the upstream sequence and the sequence deduced from amino acids, are shown in sequences SEQ ID No1 and SEQ ID No2. The single gene permitting the expression of the proteins doublet has 975 base pairs between positions 1082 and 2056, inclusive, of the nucleotide sequence.

A consensus sequence for ribosome fixation (Shine Dalgamo) was identified upstream of the gene.

The gene has a high percentage of GC of 69.4% compared with 65% 20 of GC for *M. tuberculosis.*

The protein deduced from the gene has a typical signal sequence with an ANA cleavage site for the signal peptidase.

The gene codes for a protein with 325 amino acids which includes a signal sequence of 39 amino acids.

The results obtained by biochemical analysis of the amino acid composition of the purified proteins from *M. bovis* BCG and *M. tuberculosis*compared with those deduced from the protein sequence are in good agreement (table 2). This leads to the conclusion that there is a single gene which allows the expression of proteins of two molecular weights in *Mycobacterium smegmatis* and *E. coli.*

2.2.4 Analysis of the Protein Sequence and Comparison of Sequences:

The molecular weight calculated from the deduced amino acid sequence is 28.7 kDa.

The calculated isoelectric point is 4.36. This last result is also in good agreement with biochemical determination of the isoelectric point carried out on purified *M. bovis* BCG proteins.

The deduced amino acid sequence shows a high percentage of proline and alanine (21.8% and 19.1%).

The complete sequence shows a homology with a recently described protein from *Mycobacterium leprae*. The two sequences are compared in FIG. 17. The homology score between the two proteins is 65.4%. This protein described for *Mycobacterium leprae* also has a signal sequence typical for secreted proteins.

The hydrophobicity profile of the protein deduced from *M. tuberculosis*, which is the object of the present invention (SEQ ID No2) has been established. It is shown in FIG. 18.

TABLE 1

Cloning in pUC18 of a 3 kb insert allowing expression of recombinant proteins in *E. coli.*

| pUC18: *M. tuberculosis* clones | Size of inserts | ELISA expression of proteins |
|---|---|---|
| N°34 | 3 kb | ++ |
| N°35 | 3 kb + 4 kb | + |
| N°4 | 3 kb | – |
| N°17 | 3 kb + 4 kb + 1.7 kb | – |

TABLE 2

Amino acid compositions of the 45/47 kDa proteins from *M. tuberculosis* and *M. bovis* BCG and of 27/32 kDa proteins from *M. leprae*

| | Sequence deduced (% in moles) | | Chemical analysis (% in moles) | |
|---|---|---|---|---|
| Residue | *M. leprae* | *M. tuber* | *M. tuber* | *M. bovis* BCG |
| A = Ala | 13.3 | 18.5 | 19.2 | 19.2 |
| B = Asx | — | — | 10.4 | 10.6 |
| C = Cys | 0.4 | 0 | <0.5 | <0.5 |
| D = Asp | 4.8 | 5.2 | — | — |
| E = Glu | 4.8 | 3.1 | — | — |
| F = Phe | 2.0 | 2.5 | 2.4 | 2.2 |
| G = Gly | 8.0 | 7.0 | 7.1 | 7.4 |
| H = His | 0.8 | 0.3 | 0.4 | 0.4 |
| I = Ile | 5.2 | 2.5 | 2.2 | 2.3 |
| K = Lys | 2.8 | 2.5 | 2.7 | 2.9 |
| L = Leu | 6.8 | 4.2 | 4.4 | 4.7 |
| M = Met | 0.8 | 0.7 | 0.5 | 0.5 |
| N = Asn | 4.0 | 4.5 | — | — |
| P = Pro | 13.3 | 21.7 | 20.9 | 21.9 |
| Q = Gln | 3.2 | 2.8 | — | — |
| R = Arg | 2.8 | 2.8 | 2.7 | 2.5 |
| S = Ser | 9.6 | 5.9 | 5.6 | 5.0 |
| T = Thr | 4.8 | 6.3 | 5.7 | 5.4 |
| V = Val | 8.0 | 5.9 | 6.2 | 5.8 |
| W = Trp | 1.2 | 1.4 | N.D. | N.D. |
| Y = Tyr | 2.8 | 2.1 | 2.2 | 2.2 |
| Z = Glx | — | — | 6.3 | 6.0 |

Asx = Asp + Asn
Glx = Glu + Gln

What is claimed is:

1. A hybrid protein, comprising the amino acid sequence of SEQ ID NO:2 or SEQ ID NO:3 linked to an antigenic polypeptide which is able to induce an immune response in an animal.

2. The hybrid protein of claim 1, comprising the amino acid sequence of SEQ ID NO:2 and a linked to an antigenic polypeptide which is able to induce an immune response in an animal.

3. The hybrid protein of claim 1, comprising the amino acid sequence of SEQ ID NO:3 linked to an antigenic polypeptide which is able to induce an immune response in an animal.

4. The hybrid protein of claim 1, wherein the immune response is a humoral immune response.

5. The hybrid protein of claim 1, wherein the immune response is a cellular immune response.

6. The hybrid protein of claim 1, wherein said antigenic polypeptide is a glycoprotein.

7. The hybrid protein of claim 1, wherein said antigenic polypeptide is a viral toxin.

8. The hybrid protein of claim 1, wherein said antigenic polypeptide is selected from the group consisting of a diphtheria toxin, a tetanus toxin, an HBS antigen of the HBV virus, and a VP1 antigen of the poliomyelitis virus.

9. A composition comprising the hybrid protein of claim 1.

10. A pharmaceutical composition comprising a pharmaceutically effective amount of the hybrid protein of claim 1 and a pharmaceutically compatible diluent or adjuvant.

11. A method of inducing an immune response in an animal, comprising administering the hybrid protein of claim 1 to said animal in an amount effective to induce an immune response.

12. The method of claim 11, wherein said animal is a human.

* * * * *